(12) United States Patent
Katayev et al.

(10) Patent No.: US 12,230,404 B2
(45) Date of Patent: Feb. 18, 2025

(54) METHODS FOR INDIRECT DETERMINATION OF REFERENCE INTERVALS

(71) Applicant: Laboratory Corporation of America Holdings, Burlington, NC (US)

(72) Inventors: Alexander L. Katayev, Graham, NC (US); Arren H. Fisher, Durham, NC (US); Dajie Luo, Cary, NC (US); Mark Sharp, Gibsonville, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1113 days.

(21) Appl. No.: 16/681,346

(22) Filed: Nov. 12, 2019

(65) Prior Publication Data

US 2020/0082946 A1 Mar. 12, 2020

Related U.S. Application Data

(62) Division of application No. 14/184,461, filed on Feb. 19, 2014, now Pat. No. 10,504,625.

(60) Provisional application No. 61/766,534, filed on Feb. 19, 2013.

(51) Int. Cl.
*G16H 50/70* (2018.01)
*G16H 10/40* (2018.01)
*G16H 70/00* (2018.01)

(52) U.S. Cl.
CPC ............. *G16H 50/70* (2018.01); *G16H 70/00* (2018.01); *G16H 10/40* (2018.01)

(58) Field of Classification Search
None
See application file for complete search history.

(56) References Cited

U.S. PATENT DOCUMENTS

| 10,504,625 | B2 | 12/2019 | Katayev et al. |
| 2003/0018633 | A1 | 1/2003 | Horn |
| 2008/0294350 | A1 | 11/2008 | Rosano et al. |
| 2014/0236491 | A1 | 8/2014 | Katayev et al. |

FOREIGN PATENT DOCUMENTS

| WO | 2014130562 | 8/2014 |

OTHER PUBLICATIONS

Geffré, Anne, et al. "Reference values: a review." Veterinary clinical pathology 38.3 (2009): 288-298.*
U.S. Appl. No. 14/184,461, "Final Office Action", filed Dec. 6, 2017, 21 pages.
U.S. Appl. No. 14/184,461, "Non Final Office Action", filed Mar. 23, 2017, 16 pages.
U.S. Appl. No. 14/184,461, "Non-Final Office Action", filed Jun. 4, 2018, 16 pages.
U.S. Appl. No. 14/184,461, "Non-Final Office Action", filed Jun. 26, 2019, 8 pages.
U.S. Appl. No. 14/184,461, "Notice of Allowance", filed Aug. 12, 2019, 10 pages.
U.S. Appl. No. 14/184,461, "Restriction Requirement", filed Oct. 4, 2016, 6 pages.
U.S. Appl. No. 14/184,461, "Final Office Action", filed Dec. 31, 2018, 21 pages.
Bock et al., The data warehouse as a foundation for population-based reference intervals, Am. J. Clin. Pathol., 120:662-670, 2003.
Box et al., An analysis of transformations, Journal of the Royal Statistical Society. Series B (Methodological), 26(2):211-252,1964.
CA2,900,393, "Office Action", Jan. 27, 2020, 7 pages.
Colantonio et al., Closing the gaps in pediatric laboratory reference intervals: A Caliper database of 40 biochemical markers in a healthy and multiethnic population of children, Clin. Chem., 58:854-568, 2012.
College of American Pathology, All Common Checklist 2012, COM.50000 Reference Intervals. COM.50100 Reference Interval Evaluation.
Defining, Establishing, and Verifying Reference Intervals in the Clinical Laboratory; Approved Guideline—Third Edition. CLSI document C28-A3. Wayne, PA: Clinical and Laboratory Standards Institute; 2008.
Department of Health and Human Services. The Centers for Disease Control and Prevention. National Center for Environmental Health. Second National Report on Biochemical Indicators of Diet and Nutrition in the U.S. Population; 2012.
Dorizzi et al., Indirect methods for TSH reference interval: At last fit for purpose? Am. J. Clin. Pathol., 135:167-174, 2011.
EP14712370.7, "Office Action", Mar. 26, 2019, 12 pages.
EP14712370.7, "Office Action", Oct. 24, 2018, 5 pages.
Faraway, Linear models with R, 1st ed. Boca Raton, Florida: Chapman and Hall/CRC, 2004.
Fraser, Biological variation: From principles to practice. Washington, DC: AACC Press; 2001.
Grossi et al., The REALAB Project: A new method for the formulation of reference intervals based on current data, Clinical Chemistry 51(7):1232-1240, 2005.
Hoffmann et al., "Statistics in the Practice of Medicine", The Journal of The American Medical Association, vol. 185, No. 11, XP009179447, Sep. 14, 1963, pp. 864-873.

(Continued)

*Primary Examiner* — G. Steven Vanni
(74) *Attorney, Agent, or Firm* — Kilpatrick Townsend & Stockton LLP

(57) ABSTRACT

The invention relates to methods for indirectly determining clinical laboratory reference intervals. In one aspect, a reference interval is determined using all measurements for a given analyte stored in a large existing database. In other aspects, a characteristic of a subject is used to select a reference population for inclusion in reference interval calculations. In other aspects, the invention provides methods for changing treatment plan, diagnosis, or prognosis for an individual subject based on differences between the new reference interval and a previously utilized reference interval. In other aspects, the invention provides systems and computer readable media for indirectly determining reference intervals.

16 Claims, 15 Drawing Sheets

(56) References Cited

OTHER PUBLICATIONS

Horowitz, "Defining, Establishing, and Verifying Reference Intervals in the Clinical Laboratory; Approved Guideline", CLSI, vol. 28, No. 30, 2010, pp. 1-59.

Ichirara, "An Appraisal of Statistical Procedures Used in Derivation of Reference Interval", Clinical chemistry and laboratory medicine, vol. 48, No. 11, 2010, pp. 1537-1551.

Katayev et al., "Establishing Reference Intervals for Clinical Laboratory Test Results: Is There a Better Way", American Journal of Clinical Pathology, vol. 133, No. 2, Jan. 20, 2010, pp. 180-186.

Katayev et al., "Reference Intervals Data Mining: No Longer a Probability Paper Method", American Society for Clinical Pathology, vol. 143, No. 1, Jan. 2015, pp. 134-142.

Kestin, "Statistics in Medicine", Anaesthesia & Intensive Care Medicine, vol. 13, No. 4, Apr. 2012, pp. 181-188.

Lott et al., Estimation of reference intervals for total protein in cerebrospinal fluid, Clin. Chem., 35:1766-1770, 1989.

PCT/US2014/017177, "International Search Report and Written opinion", Aug. 7, 2014, 13 pages.

Reiber, External quality assessment in clinical neurochemistry: survey of analysis for cerebrospinal fluid (CSF) proteins based on CSF/serum quotients, Clin. Chem., 41:256-263, 1995.

Ricos et al., Current databases on biologic variation: pros, cons and progress, Scand. J. Clin. Lab. Invest., 59:491-500, 1999.

Shaw, J. et al., Validity of establishing pediatric reference intervals based on hospital patient data: A comparison of the modified Hoffmann approach to Caliper reference intervals obtained in healthy children, University of Toronto, Laboratory Medicine and Pathobiology, 2012, Poster.

Siest, et al., The theory of reference values: an unfinished symphony, Clin. Chem. Lab. Med., 51:47-64, 2013.

Soldin et al., "Pediatric Reference Intervals", 6th ed. Washington, DC: AACC Press, 2007.

Stoop, et al., Quantitative proteomics and metabolomics analysis of normal human cerebrospinal fluid samples, Mol. Cell. Proteomics, 9:2063-2075, 2010.

\* cited by examiner

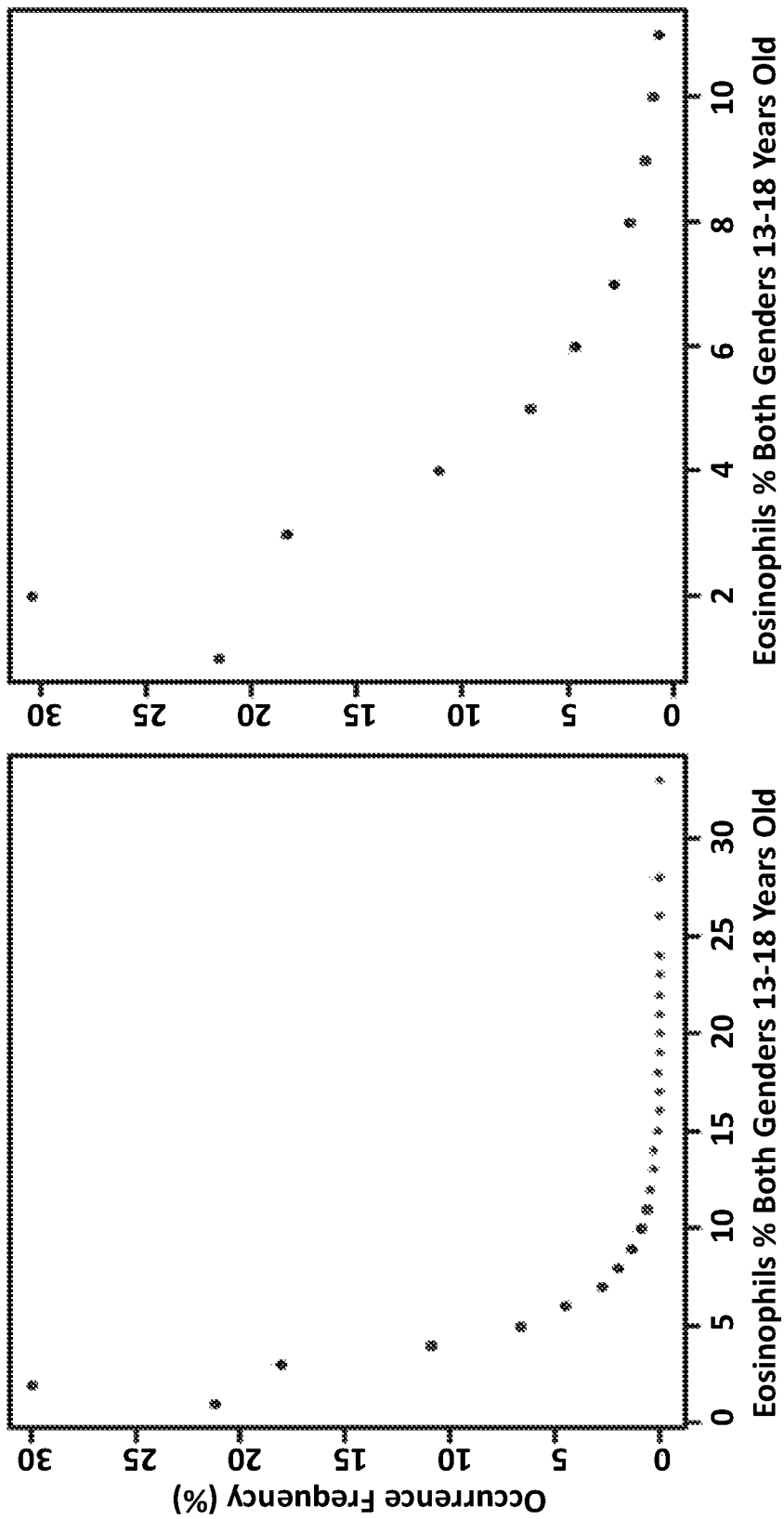

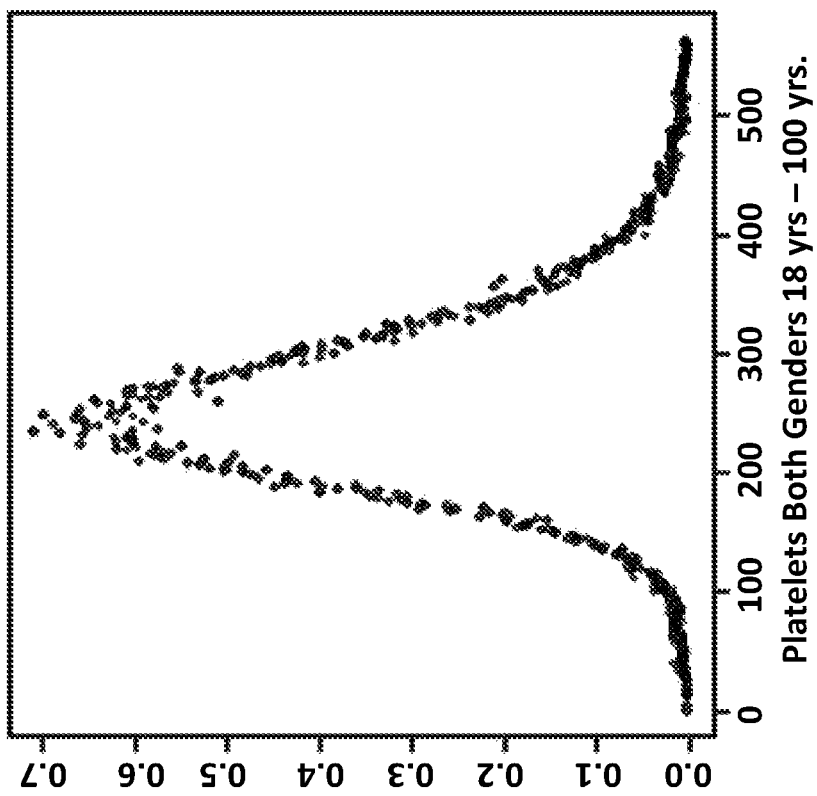
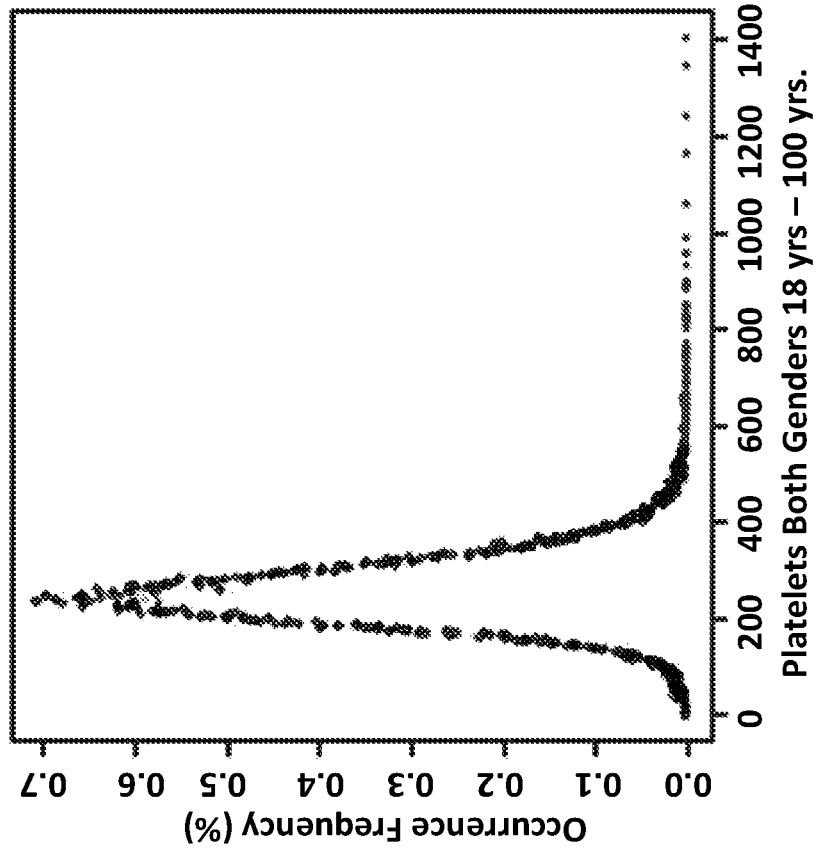
FIG. 10A
FIG. 10B

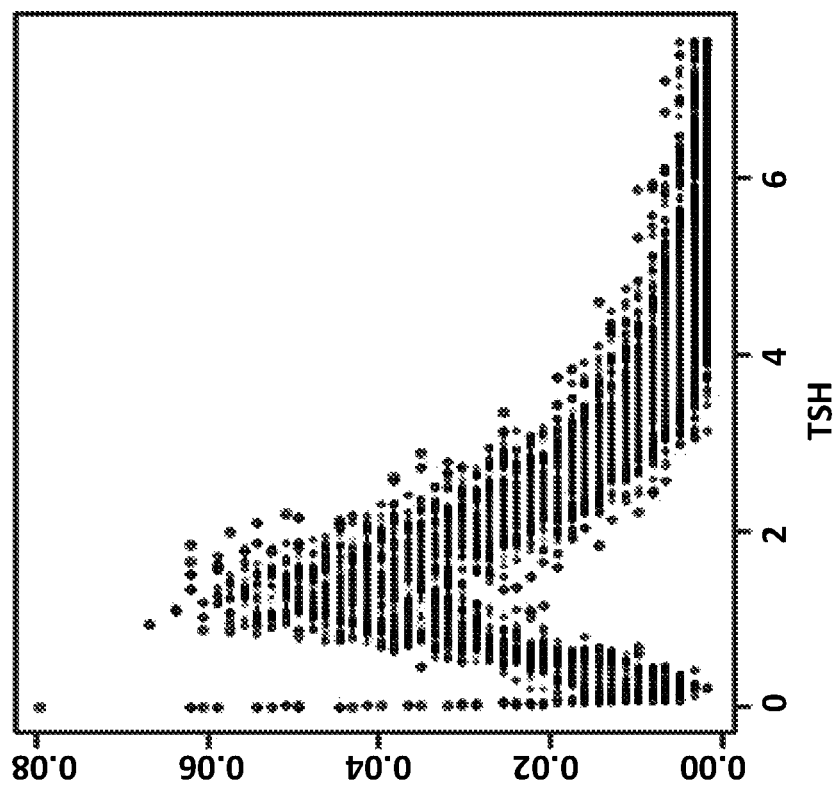
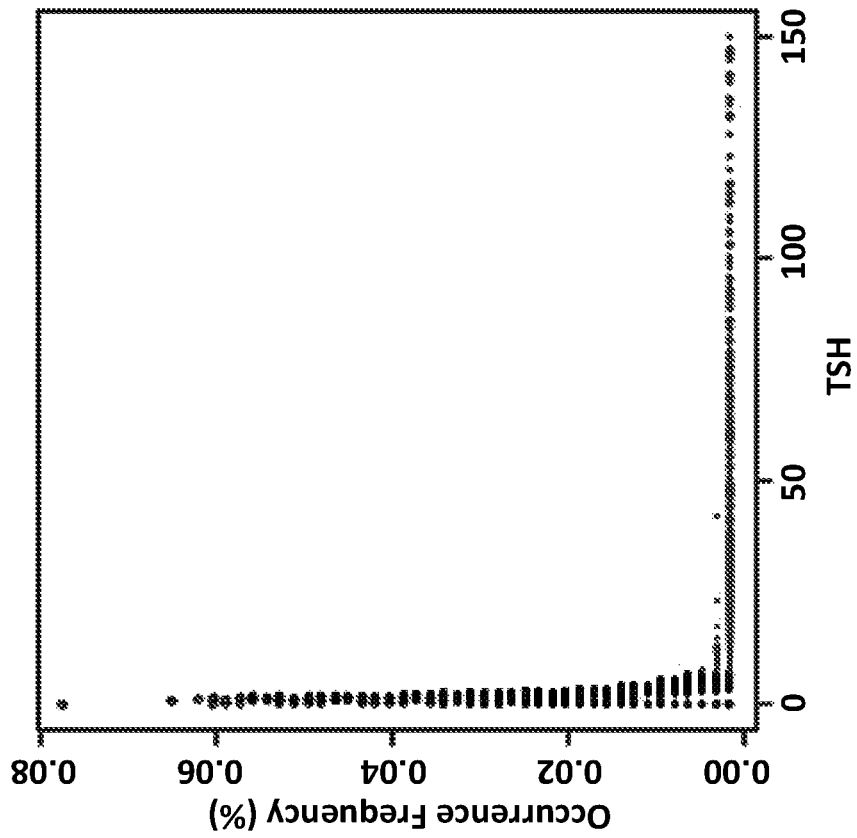

METHODS FOR INDIRECT DETERMINATION OF REFERENCE INTERVALS

RELATED APPLICATIONS

This application is a Divisional application of U.S. Nonprovisional application Ser. No. 14/184,461, filed Feb. 19, 2014, which claims priority of U.S. Provisional application 61/766,534, filed Feb. 19, 2013. All of the foregoing applications are incorporated herein by reference in their entirety.

FIELD OF THE INVENTION

The present invention relates to methods for indirect determination of reference intervals for clinical laboratory testing using data from existing laboratory databases.

BACKGROUND

A reference interval provides information about a range of measurements observed in the reference population to assist health care providers in interpretation of individual clinical laboratory test results.

Existing regulations require laboratories to provide reference intervals on test result reports and review/revise those intervals on regular basis. Many laboratories adopt reference intervals from other sources, such as other laboratories, manufacturers of testing reagents, or previously published studies. In 2008, the Clinical and Laboratory Standards Institute-approved guideline recognized the reality that, in practice, very few laboratories perform their own reference interval studies, instead referring to studies done many decades ago, when both the methods and the population were very different. (Defining, Establishing, and Verifying Reference Intervals in the Clinical Laboratory; Approved Guideline. Third Edition. CLSI document C28-A3. Wayne, PA: Clinical and Laboratory Standards Institute; 2008). Thus, it is apparent that many reference intervals which have been reported for decades may not currently be accurate for a given laboratory due to differences in modern testing methodology and/or the population serviced.

There are a number of additional problems contributing to resistance or reluctance to change current practice. Conducting independent de novo studies for reference interval determinations using the conventional direct donor sampling method is expensive and has limitations and complications. The studies typically recruit healthy subjects, whereby criteria must be defined for determining which subjects are "healthy."

Recruiting and obtaining informed consent from candidate subjects and excluding subjects with subclinical diseases can be difficult and expensive. Moreover, the healthy reference populations likely include subjects with subclinical disease. Even successful studies of this type have relatively low sample sizes (e.g. about 100-150 individuals), such that statistical power is lacking. It is statistically more robust to analyze thousands of measurements that include a number of unhealthy subjects than 120 subjects assumed to be healthy. Large sample size is essential for accuracy in determination of reference intervals.

An indirect method of reference interval estimation that used test results already stored in the laboratory database was described by Hoffmann in 1963 (Hoffmann, R G. Statistics in the Practice of Medicine. JAMA, 185: 864-873, Sep. 14, 1963). Hoffmann described a method using manual plotting of test data on graph paper and visual assessment of the graph for reference interval estimation. It was limited by subjectivity of visualization and manual data manipulations. Manual and semi-manual data manipulations using Hoffmann's method were also used in later publications (Soldin et al. Pediatric Reference Intervals, AACC Press, 6th edition).

To better serve the healthcare industry, the clinical laboratory industry is in need of robust and reliable methodology for determination and verification of reference intervals for clinical laboratory test results.

SUMMARY

Certain aspects of the present invention provide a method for indirectly determining a reference interval for an analyte, comprising: (a) pooling data from an existing database of measurements of the analyte from a selected reference population; (b) plotting cumulative frequencies of data against a range of analyte measurements from the data of the selected reference population to determine a distribution of the data; (c) applying a transformation to normalize data if the distribution is significantly skewed; (d) calculating a linear regression of the plotted data; and (e) determining a reference interval for the analyte in the reference population by selecting a range that corresponds to the linear portion of the curve.

Other aspects of the present invention provide a method for providing a reference interval for an analyte to aid in evaluation of an individual subject's test result for the analyte, comprising: (a) selecting a reference population from an existing database based on at least one characteristic of the subject; (b) pooling data from the database for measurements of the analyte from the reference population; (c) plotting cumulative frequencies of data against a range of analyte measurements from the reference population; (d) applying a transformation to normalize distribution if the initial distribution is significantly skewed; (e) calculating a linear regression of the plotted data; and (f) selecting the linear portion of the curve to determine a reference interval for the analyte in the reference population. In some embodiments, such a reference interval may be used in a method further comprising: providing a biological sample from a subject having the characteristic(s) used to select the reference population; determining a measurement of the analyte in the biological sample; and comparing the measurement of the analyte in the biological sample to the reference interval.

In other aspects, the invention provides computer readable media for determining a reference interval according to the method described, the computer readable media comprising: (a) program code for selecting analyte data for a specific reference population from an existing database; (b) program code for plotting cumulative frequencies of the data against the measurement of analyte; (c) program code for calculating a linear regression equation of the plotted data; (d) program code for applying a transformation to normalize distribution if the initial distribution is significantly skewed; and (e) program code for selecting the linear portion of the curve to determine a reference interval for the analyte in the reference population.

In other aspects, the invention provides a system for determining a reference interval, comprising: (a) a component for pooling data from an existing database of measurements of the analyte from a selected reference population; (b) a component for plotting cumulative frequencies of data against a range of analyte measurements from the data of the selected reference population to determine a distribution of the data; (c) a component for applying a transformation to normalize data if the distribution is significantly skewed; (d) a component for calculating a linear regression of the plotted data; and (e) a component for determining a reference interval for the analyte in the reference population by selecting a range that corresponds to the linear portion of the curve.

Other aspects of the invention are provided below.

BRIEF DESCRIPTION OF THE FIGURES

FIG. 4A-4B is a graphical illustration of the data for eosinophils in subjects 13-18 years old in Example 1 according to an embodiment of the invention, where FIG. 4A shows all data and FIG. 4B shows data with outliers removed.

FIG. 6A shows all data and FIG. 6B shows data with outliers removed.

FIG. 7A shows all data and FIG. 7B shows data with outliers removed.

FIG. 9A shows all data and FIG. 9B with outliers removed.

FIG. 10A-10B is a graphical illustration of data for platelets in subjects age 18-100 years old in Example 3 according to an embodiment of the invention, where the data is selected from the database at a later time point. FIG. 10A shows all data and FIG. 10B with outliers removed.

FIG. 11A shows linear regression for the early time point and FIG. 11B for the later time point.

FIG. 12A shows data before transformation and FIG. 12B after BoxCox transformation.

FIG. 13A shows linear regression of data without transformation, and FIG. 13B shows linear regression of data after BoxCox transformation.

FIG. 14A-14B is graphical illustration of data for thyroid stimulating hormone (TSH) in all subjects in Example 5 according to an embodiment of the invention. FIG. 14A shows all data and FIG. 14B with outliers removed.

DETAILED DESCRIPTION

Figure 1:
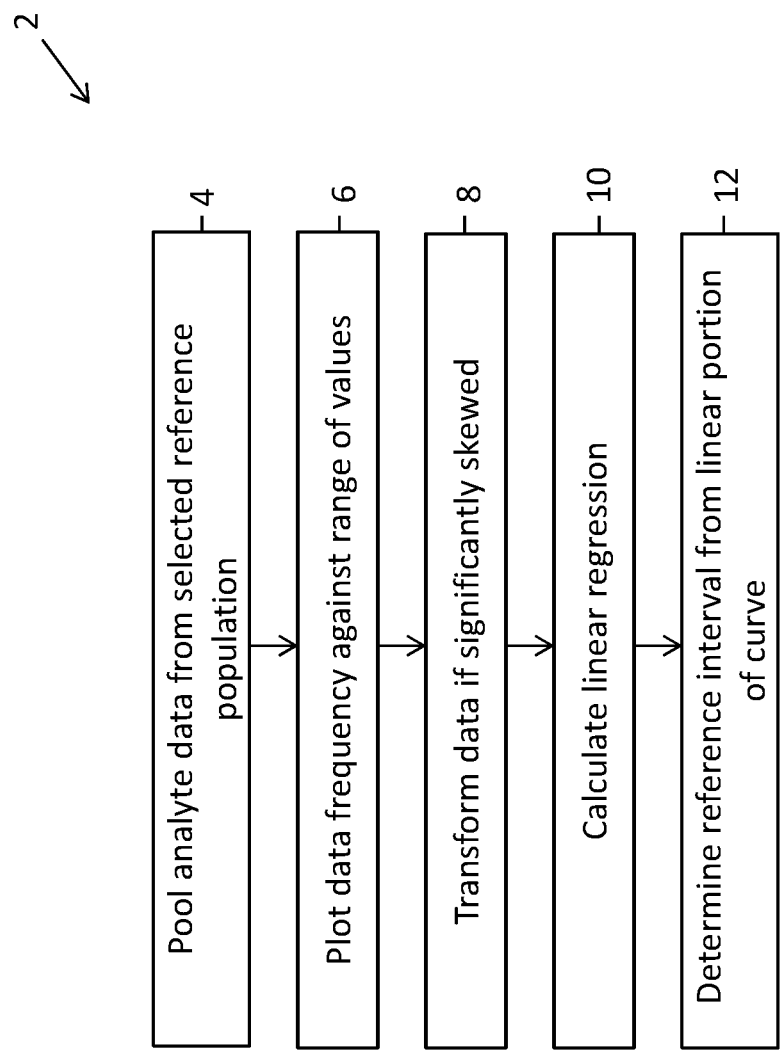
FIG. 1 is a schematic illustration of a method for determining a reference interval for an analyte according to an embodiment of the invention.

The following description recites various aspects and embodiments of the present invention. No particular embodiment is intended to define the scope of the invention. Rather, the embodiments merely provide non-limiting examples of various methods and systems that are at least included within the scope of the invention. The description is to be read from the perspective of one of ordinary skill in the art; therefore, information well known to the skilled artisan is not necessarily included.

Definition and Abbreviations

The following terms, unless otherwise indicated, shall be understood to have the following meanings:

As used herein, the terms "a," "an," and "the" can refer to one or more unless specifically noted otherwise.

The term "or" is not to be construed as identifying mutually exclusive options. For example, the phrase "X contains A or B" means that X contains A and not B, X contains B and not A, or X contains both A and B. That is, the term "or" is used to mean "and/or" unless explicitly indicated to refer to alternatives only or the alternatives are mutually exclusive, although the disclosure may support a definition that refers to only alternatives and "and/or." As used herein "another" can mean at least a second or more.

As used herein, the terms "subject," "individual," and "patient" are used interchangeably. The use of these terms does not imply any kind of relationship to a medical professional, such as a physician.

As used herein, the term "reference population" is used to refer to all the subjects having measurements for an analyte of interest within a database whose data are selected for inclusion in the calculation of a reference interval. The entire population represented in the database may be included, or specific characteristics of the subjects may be selected for inclusion, to filter the data for determination of a specific reference interval.

As used herein, the term "reference interval" refers to a central range of measurements for an analyte that is observed in a reference population and reported by a laboratory along with an individual test result to aid a health care provider in interpretation of that individual result. Typically (but not necessarily), a reference interval has referred to the central 95% of values obtained from the reference population of subjects.

As used herein, the term "biological sample" is used to refer to any fluid or tissue that can be isolated from an individual. For example, a biological sample may be whole blood, plasma, serum, other blood fraction, urine, cerebrospinal fluid, tissue homogenate, saliva, amniotic fluid, bile, mucus, peritoneal fluid, lymphatic fluid, perspiration, tissues, tissue homogenate, buccal swabs, chorionic villus samples, and the like.

As used herein, the term "like biological sample" is used to refer to comparisons between the same types of biological samples described above. For example, a measurement of analyte in a blood sample is compared to a reference interval determined from measurements of the analyte in other blood samples.

As used herein, the term "analyte" is used to refer to a substance of interest in an analytical procedure. It is the substance being analyzed in the biological sample.

As used herein, the terms "normal distribution" or "Gaussian distribution" refers to a continuous probability distribution, also known as the bell-shaped curve. "Skewed distribution," by contrast, as used herein refers to a probability distribution in which an unequal number of observations lie below or above the mean and the curve is not bell-shaped (see e.g., FIGS. 12 and 13). The terms "skewed distribution" and "significantly skewed" distribution will be understood to those skilled in the art. In some embodiments, significantly skewed refers to a dataset where the mean is located in the first or fifth quintile of the distribution.

As used herein, the term "characteristic" refers to any feature or trait that can distinguish sub-groups of subjects within the entire starting reference population for inclusion in the specific reference population. For example, age, gender, race, and geographic location are characteristics that may be designated in a reference population. A more specific reference population corresponds to a more individualized reference interval.

Methods for Determining Reference Intervals

Certain aspects of the present invention provide a method for indirectly determining a reference interval for an analyte, comprising: (a) pooling data from an existing database of measurements of the analyte from a selected reference population; (b) plotting cumulative frequencies of data against a range of analyte measurements from the data of the selected reference population to determine a distribution of the data; (c) applying a transformation to normalize data if the distribution is significantly skewed; (d) calculating a linear regression of the plotted data; and (e) determining a reference interval for the analyte in the reference population by selecting a range that corresponds to the linear portion of the curve.

In some embodiments, maximum allowable error is restricted to account for a known individual biological variation for the analyte in selecting the range that corresponds to the linear portion of the curve. In some embodiments, the selected reference population includes at least 100, 120, 140, 160, 180, 200, 220, 240, 260, 280, 300, 320, 340, 360, 380, 400, 500, 600, 700, 800, 900, 1,000, 1,500, 2,000, 4,000, 6,000, 8,000, 10,000, 15,000, 20,000, 40,000, 60,000, 80,000, or 100,000 different individuals.

Other aspects of the present invention provide a method for providing a reference interval for an analyte to aid in evaluation of an individual subject's test result for the analyte, comprising: (a) selecting a reference population from an existing database based on at least one characteristic of the subject; (b) pooling data from the database for measurements of the analyte from the reference population; (c) plotting cumulative frequencies of data against a range of analyte measurements from the reference population; (d) applying a transformation to normalize distribution if the initial distribution is significantly skewed; (e) calculating a linear regression of the plotted data; and (f) selecting the linear portion of the curve to determine a reference interval for the analyte in the reference population. In some embodiments, such a reference interval may be used in a method comprising: providing a biological sample from a subject having the characteristic(s) used to select the reference population; determining a measurement of the analyte in the biological sample; and comparing the measurement of the analyte in the biological sample to the reference interval.

In some embodiments, the selected reference population includes at least 100, 120, 140, 160, 180, 200, 220, 240, 260, 280, 300, 320, 340, 360, 380, 400, 500, 600, 700, 800, 900, 1,000, 1,500, 2,000, 4,000, 6,000, 8,000, 10,000, 15,000, 20,000, 40,000, 60,000, 80,000, or 100,000 different individuals. In some embodiments, a different course of treatment, diagnosis, or prognosis is determined or selected for the subject based on the reference interval as compared to the course of treatment, diagnosis, or prognosis using a different reference interval previously utilized for the same analyte. In some embodiments, the reference population is selected according to at least two characteristics of the individual subject.

FIG. 1 illustrates a method for determining a reference interval for an analyte according to an embodiment of the invention. In this method (2), analyte data is pooled from a selected reference population (4). The data is plotted against the range of measurement values represented (6), and at least one transformation is applied if the data is initially significantly skewed (8). A linear regression of the data is calculated (10), and the reference interval is determined from the linear portion of the resulting curve (12).

Figure 2:
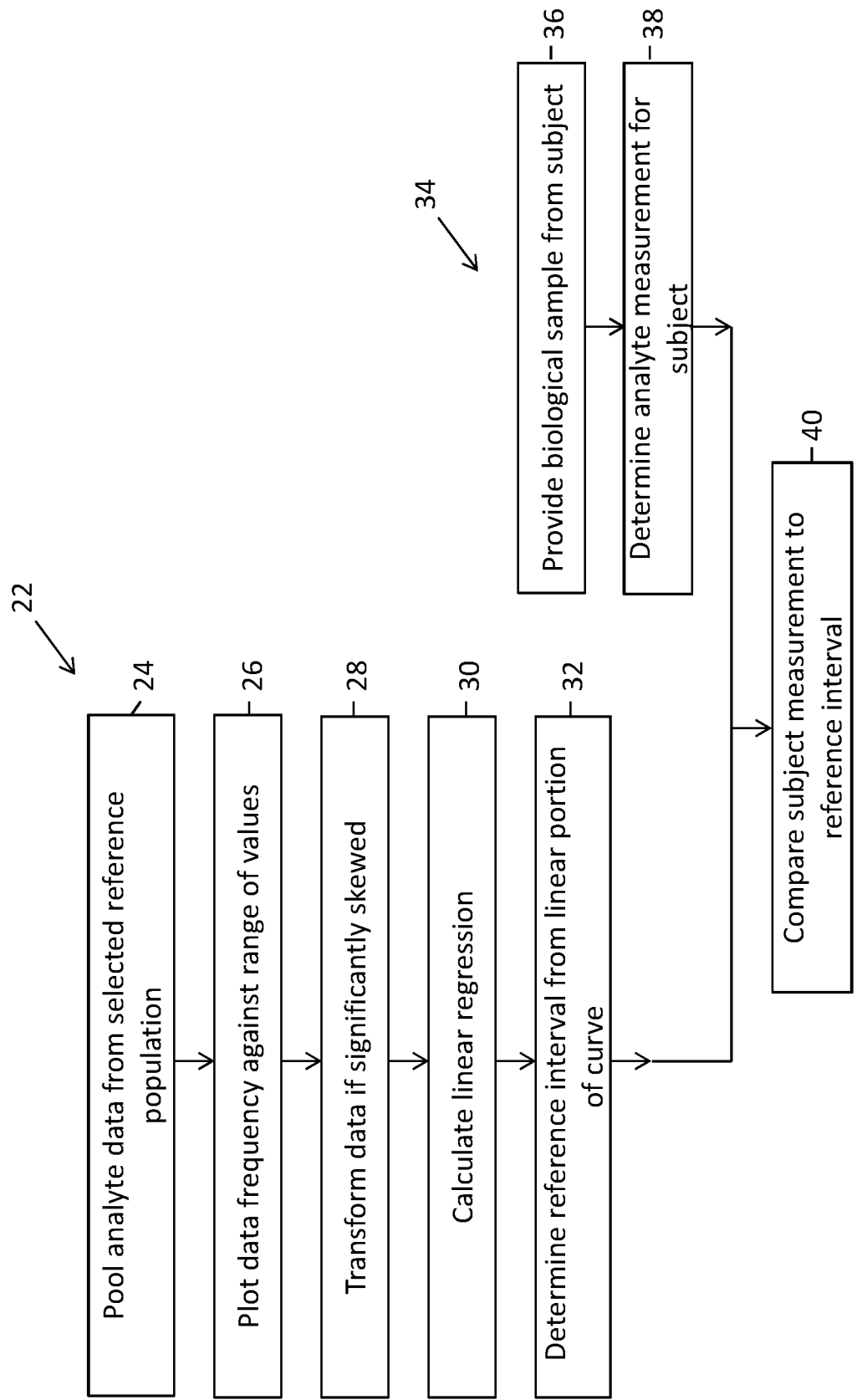
FIG. 2 is a schematic illustration of a method for determining a reference interval based on at least one characteristic of an individual subject, according to an embodiment of the invention.

FIG. 2 illustrates a method for determining a reference interval based on at least one characteristic of an individual subject, according to an embodiment of the invention. In this method (22), analyte data is pooled from a reference population that is based on at least one characteristic of an individual test subject as represented by asterisk * (24). The data is plotted against the range of measurement values represented (26), and at least one transformation is applied if the data is initially significantly skewed (28). A linear regression of the data is calculated (30), and the reference interval is determined from the linear portion of the resulting curve (32). This individualized reference interval may then be used to evaluate the analyte in an individual subject. In this method (34), a biological sample from the individual subject is provided (36) and the analyte is measured in the sample (38).

Analytes

In some embodiments, the invention provides a method for indirectly determining a reference interval for an analyte using data from an existing database having a large number of measurements of that analyte. In some embodiments, the invention provides a method for determining an analyte reference interval for evaluating a laboratory test result. In some embodiments, the invention provides a method for determining an analyte reference interval to aid in evaluating a laboratory test result. In some embodiments, the invention provides a method for determining an analyte reference interval to aid in making a medical decision. In some embodiments, the invention provides a method for verification of existing laboratory reference intervals.

The analyte may be any substance (such as a biomolecule or compound), parameter, ratio, or other relationship that is measurable within the body or in biological samples removed from the body, such as those described above. The invention is not limited to any particular analyte or set of analytes.

In some embodiments, analytes include hormones, lipids, proteins, nucleic acids, or combinations or fragments thereof. In some embodiments, the analytes are small molecules such as creatinine, ATP, or glucose. In some embodiments, the analytes are larger entities such as platelets or red blood cells (such as hematocrit).

In some embodiments, analytes include polypeptides or oligopeptides, including antibodies or antibody fragments. In some such embodiments, the peptides or oligopeptides are indicative of a likelihood of showing responsiveness or resistance to a course of treatment, such as a drug-based course of treatment.

In some embodiments, the analytes include viruses or biomarkers indicative of infection. In some embodiments, the analytes include antibodies (or fragments thereof), such as antibodies or antibody fragments that are indicative of human allergic responses, e.g., human IgE antibodies, or are indicative of immuno-rejection during organ transplant, or are indicative of the efficacy of a vaccination protocol, or are antibodies related to cellular signaling.

In some embodiments, the analytes include biomarkers, such as biomarkers indicative of a disease or condition, e.g., an autoimmune disease. In some embodiments, the biomarkers may include biological measurements unrelated to chemistry, e.g. height, weight, skull dimensions, etc. In some embodiments, the analytes include bacteria or parasites. In some embodiments, the analytes include polynucleotides that are indicative of adverse drug reactions. The analytes can also include biomarkers for various diseases, cytokines, chemokines, and growth factors. They can also include small molecules, such as steroid hormones and inorganic molecules such as salts and other electrolytes.

Indirect Sampling of Specific Populations

In some embodiments, the invention provides a method for indirectly determining a reference interval for an analyte from an existing database containing a large number of measurements of that analyte. Larger sample sizes correspond to higher statistical power. In some embodiments, the majority of the database comprises data from an outpatient population rather than a population associated with a hospital by including only the data for tests ordered from non-acute settings. In some embodiments, the invention provides a method for verification of an existing laboratory reference interval.

In some embodiments, the invention provides a method for determining an individualized reference interval. In some embodiments, the invention provides a method for determining an updated individualized reference interval. In some embodiments, the invention provides a method for determining a sub-population reference interval. In some embodiments, the invention provides a method for determining an updated reference interval essentially concurrent with generation of the individual lab test report. In some embodiments, the invention provides a method for determining an updated global reference interval.

In some embodiments, the reference interval is individualized based on at least one characteristic of the subject of interest. According to a preferred embodiment of the invention, there is no need to define "healthy" or parse healthy subjects from unhealthy subjects. In some embodiments, the invention provides a method for selecting a specific reference population from the database. In some embodiments, the reference population is restricted based on multiple characteristics; this can generate a more individualized reference interval. In some embodiments, the data is filtered according to specific characteristics of interest to achieve a desired reference population. For example, only data from female subjects are included, or only subjects in a specific age range, or both. Any number of characteristics may be used to narrow the reference population.

In some embodiments, the data is used only from the subjects on whom the test of interest was ordered in combination with another specific test. In certain embodiments the data is used when results for the other test meet predefined criteria (e.g. the result is within the predefined limits). In some embodiments, it may be desirable for the reference population to be geographically restricted. For example, as described in more detail herein, measurements of hemoglobin from subjects in areas with high elevation (e.g. Colorado) are significantly different than from subjects at sea level. In this manner, mining the database for a more specific reference population can provide a more individualized reference interval. In such embodiments, resources are not wasted on determining who is healthy or unhealthy. Data is extracted for all subjects who meet the designated reference population criteria.

Statistical Methods

In some embodiments, the invention provides statistical methods for analysis of analyte data from a specific reference population. In some embodiments, the invention provides methods for plotting data and removing outliers from the reference population dataset. In some embodiments, the invention provides methods for calculating linear regression of the plotted data. In other embodiments, the invention provides a method in which a transformation is applied to normalize distribution if the initial distribution is non-Gaussian.

In some embodiments, the invention allows the user to account for biologic variation of analytes by setting a maximum allowable error at the linear regression step, such that the reference interval has increased clinical relevance and reflects the reference population with respect to normal physiological variation of the analyte of interest and does not exclude a significant number of subjects in the reference population. As described in more detail below, in some embodiments the reference interval does not exclude greater than 2.5% from both upper and lower limits when central 95% is used. In some embodiments, the linear portion of the linear regression curve is selected to derive a reference interval for the analyte in the reference population.

In some embodiments, the reference interval is provided to a health care provider for assistance in evaluating the analyte measurement for a particular subject. In some embodiments, following selection of the reference population, numerical laboratory test results for the given analyte that are stored in the laboratory database are loaded in the program data source. Where multiple laboratories or databases are networked, data may be loaded from only one location or from two or more locations.

In some embodiments, data are rounded to a specified number of decimal places. In some embodiments, outlying observations may be removed. In some embodiments the outliers are removed using Chauvenet criteria. Other outlier removing statistical methods that may be used include, but are not limited to, Dixon test, Tukey method, and Barnett and Lewis technique. Or, other methods known in the art may be used. With Chauvenet criteria, a measurement is eliminated if the probability of its occurrence is less than $1/(2N)$ given a normal distribution, where N is the number of measurements in the data pool and is greater than 4.

In detail, for a particular measurement $x_0$, if $$\mathrm{Prob}(X<x_0)<1/(2N) \text{ or } \mathrm{Prob}(X>x_0)<1/(2N)$$

then $x_0$ is an outlier and is excluded from further calculations on the data pool.

In some embodiments, the number of measurements (N) may be updated by the remaining observations in the data pool and the mean of the measurements in the data pool is recalculated. The Chauvenet analysis may then be repeated and, if additional outliers are identified, these outliers can be excluded from further calculations. The application of the Chauvenet criteria may be repeated until no additional outliers are identified in the remaining data pool.

In some embodiments, following the elimination of outliers, the cumulative frequency for each test result is determined. The frequency of a test result may be taken as the number of times a result occurs in the data set divided by the total number of results $$F_{X_i} = \frac{Count_{X_i}}{Count_{data-pool}} \times 100\%,$$

such that the cumulative frequency is $$CF_{X_i} = \sum_{k=2}^{i} F_{X_K}$$

ordered by X.

In some embodiments, linear regression may be calculated according to Cook's distance, an exhaustive method, or other methods known in the art.

For example, in the Cook's distance method, the algorithm first fits a linear regression with all the data points. For each iteration, the Cook's statistic is calculated for the starting point and ending point. The point with the larger Cook's statistic is eliminated for the next iteration. The endpoint to remove incrementally to search for a linear region that satisfies the maximum residual error constraint, as above. The exhaustive method may search every possible subset of the population.

In some embodiments, linear regression is computed with test values plotted on Y-axis and cumulative frequency plotted on X-axis. In such embodiments, the reference intervals are determined from the linear regression equation following extrapolation of the regression line. The best-fitting linear regression ($y_i = \alpha^* x_i + \beta + \varepsilon_i$) equation may be determined by least-squares analysis ($\alpha$ is the slope, $\beta$ is the intercept of the line and $\varepsilon_i$ is the error). The line with the minimum sum of square residual values is identified accordingly. A residual value ($r_i$) is taken as the difference between the measured value ($y_i$) and the approximated one as determined by the linear regression function ($f(x_i)$), where $r_i = y_i - f(x_i)$.

In some embodiments, the linear portion of data is selected when the maximum residual error is less than a specified threshold. The chosen maximum residual error should be equal to the reported or estimated within-individual biological variation for the given analyte. The table below represents an example of the biological variation database specifications derived from publications by Ricos et al. and within-person biological variation data (CVw) that is used for the definition of the maximum allowable error (Ricos C, Alvarez V, Cava F, Garcia-Lario J V, Hernandez A, Jimenez C V, Minchinela J, Perich C, Simon M. Current databases on biologic variation: pros, cons, and progress. Scand. J. Clin. Lab. Invest. (1999) 59: 491-500. Most recently updated in 2010).

Maximum residual error (CVw) is derived from biological variation database specifications:

| Sample Type | Analyte | Biological Variation | | Desirable Specification | | | | Minimum Allowable Specifications | | | |
|---|---|---|---|---|---|---|---|---|---|---|---|
| | | CVw (%) | CVg (%) | I(%) | B(%) | TE(%) | RCV (%) | I(%) | B(%) | TE(%) | RCV (%) |
| S- | 11-Desoxycortisol | 21.3 | 31.5 | 10.7 | 9.5 | 27.1 | 66.0 | 16.0 | 14.3 | 40.6 | 73.8 |
| S- | 17-Hydroxyprogesterone | 19.6 | 52.4 | 9.8 | 14.0 | 30.2 | 60.7 | 14.7 | 21.0 | 45.3 | 67.9 |
| U- | 4 OH-3 methoxl-Vanil mandelic acid (VMA) | 22.2 | 47.0 | 11.1 | 13.0 | 31.3 | 68.8 | 16.7 | 19.5 | 47.0 | 76.9 |
| S- | 5'Nucleotidase | 11.3 | 12.6 | 5.7 | 4.2 | 13.6 | 35.1 | 8.5 | 6.3 | 20.3 | 39.1 |
| U- | 5'-Hydroxyindolacetate, concentration | 20.3 | 33.2 | 10.2 | 9.7 | 26.5 | 62.9 | 15.2 | 14.6 | 39.7 | 70.3 |
| S- | a1-Acid Glycoprotein | 11.3 | 24.9 | 5.7 | 6.8 | 16.2 | 35.1 | 8.5 | 10.2 | 24.2 | 39.1 |
| S- | a1-Antichymotrypsin | 13.5 | 18.3 | 6.8 | 5.7 | 16.8 | 41.9 | 10.1 | 8.6 | 25.3 | 46.7 |
| S- | a1-Antitrypsin | 5.9 | 16.3 | 3.0 | 4.3 | 9.2 | 18.3 | 4.4 | 6.5 | 13.8 | 20.4 |
| S- | a1-Globulin | 11.4 | 22.6 | 5.7 | 6.3 | 15.7 | 35.3 | 8.6 | 9.5 | 23.6 | 39.5 |
| U- | a1-Microglobulin, concentration, first morning | 33.0 | 58.0 | 16.5 | 16.7 | 43.9 | 102.2 | 24.8 | 25.1 | 65.9 | 114.3 |

I (Desirable) = 0.5*CVw  
B (desirable) = 0.250*(CVw² + CVg²)^{1/2}  
I (minimum allowable) = 0.75*CVw  
B (minimum allowable) = 0.375*(CVw² + CVg²)^{1/2}  
TE = 1.65*I + B  
RCV = 2^{1/2} * Z * (I² + CVw²)^{1/2} For 95% probability: Z = 1.96

Abbreviations:
CVw = within-subject biologic variation (%)
CVg = between-subject biologic variation (%)
I = specification for allowable imprecision (%)
B = specification for allowable inaccuracy (%)
TE = specification for allowable total error (%)
RCV = reference change value (%)

iteration is repeated until the iteration's maximum residual error is equal or smaller compared to the threshold maximum residual error, and this determines the linear portion.

Other methods that measure a single point's influence on regression parameters include DFFITS, COVRATIO, and DFBETAS. These methods may be used to determine which In some embodiments, the optimal linear portion may be selected as a continuous subset of the data pool that both satisfies maximum residual error constraint from the linear regression equation and satisfies the condition that the same subset includes the maximum percent of the population from the data pool.

In such embodiments, a continuous subset of the population will include all test results between the minimum and maximum test result in the subset. The percent of the test population represents a ratio of the results within the minimum and maximum result, inclusive of the end points, compared to all test results minus the outlier test results. Among all subsets that yield linear regression coefficients that satisfy the maximum residual error constraint, the subset that represents the maximum percent of the population is held as the optimal linear region because it is the linear region that represents the largest subset of the population.

Reference intervals typically encompass the central 95% of the reference population.

The reference interval (RI) may be calculated (for central 95%, x=2.5% and 97.5%):

$$RI_{min}=\alpha*2.5+\beta, RI_{max}=\alpha*97.5+\beta$$

Or, larger or smaller reference intervals (e.g. a central 90% with x=5% and 95%) may be determined accordingly. In some embodiments, the reference interval may span the central 99%, 98%, 97.5%, 95%, 94%, 93%, 92%, 91%, 90%, 85%, 80%, 75%, 70%, 65%, 60%, 55%, or 50% of the data pool.

In some embodiments, confidence intervals may be calculated for the limits of the reference interval. Non-limiting examples of confidence intervals include 99.9%, 99.5%, 99%, 98%, 97%, 96%, 95%, 94%, 93%, 92%, 91%, 90%, 85%, 80%, 75%, 70%, 65%, 60%, 55%, or 50%. The 95% confidence intervals may be calculated for both, upper and lower limits of the calculated reference interval as follows.

The 95% confidence interval for the prediction of a future observation valued $x_0$ may be calculated as, $$\hat{y}_0 \pm t_{n-2}^{0.025} \hat{\sigma} \sqrt{1+x_0^T(X^TX)^{-1}x_0}$$

Where $\hat{y}_0$ is the predicted value at $x_0$, t is the critical value of T distribution with degree of freedom (n−2), $\hat{\sigma}$ is residual standard deviation.

In some embodiments, when the source data distribution is initially significantly skewed or shows a non-Gaussian distribution, then Box-Cox transformation or another transformation known in the art may be applied as described below with back-transformation after the linear portion is calculated from the transformed data as described below. In some embodiments, the initial distribution is assessed without any transformation. In such embodiments, the mean and median are calculated for the entire dataset and the operator determines whether the mean is far enough from the median to consider the data significantly skewed. In some embodiments, the initial source data distribution is significantly skewed if the mean falls in the first or fifth quintile of the distribution. In some embodiments, the initial source data distribution is significantly skewed if the mean falls in the second or fourth quintile of the distribution. In some embodiments, most or all known transformations are applied to skewed data until the optimal transformation is identified. In some embodiments, the BoxCox method provides optimal transformation. In such embodiments, the operator determines whether or not to use the Box-Cox transformation or another known transformation. When the Box-Cox transformation is selected, the transformation addresses the assumption of a normal distribution by minimizing the heteroscedasticity in the transformed data. Objectively, it is sufficient to always apply the Box-Cox transformation here, though it may complicate interpreting the results. Further, the Box-Cox transformation method may determine that the heteroscedasticity is already at the minimal level and not transform the data. Thus, the invention also provides an unexpected method by which analyte datasets that demonstrate non-Gaussian distribution may be analyzed to generate a reference interval.

Box-Cox transformation method transforms the value x to $y_\lambda(x)$ as $$y_\lambda(x) = \begin{cases} \frac{x^\lambda - 1}{\lambda}, & \lambda \neq 0 \\ \log(x), & \lambda = 0 \end{cases}$$

$\lambda$ is chosen using maximum likelihood.

Since these transformations are not defined for negative or zero values, the following equations may be used to add a suitable quantity, c, to all of the values if a zero or negative value is encountered $$x_i = x_i + |x_{min}| \times 1.1 \text{ Negative Response}$$

$$x_i = x_i + 1 \text{ Zero Response}$$

When Box-Cox transformation is included in the process, it is applied to the data pool after the outlier removal process. The rest of the workflow process from this point is identical until the final back-transformation.

Finally, if transformation is used, the reference interval and corresponding confidence intervals need to be back-transformed to the original units by applying the inverse function of the Box-Cox transformation.

$$x = \begin{cases} (\lambda y + 1)^{1/\lambda} - c, & \lambda \neq 0 \\ e^y - c, & \lambda = 0 \end{cases}$$

In some embodiments, it is desirable to calculate standard deviation, mean, mode, and median for the linear portion of the data as well as the entire reference data set. In some embodiments it is desirable to calculate the % of data above and below the limits of the new and old (if applicable) reference intervals.

Computer Readable Media

In some embodiments, the invention provides computer readable media for determining a reference interval according to the method described, the computer readable media comprising: (a) program code for accepting input and loading from an existing database selected analyte measurement data from a specific reference population; (b) program code for plotting cumulative frequencies of the data against the analyte measurements; (c) program code for calculating a linear regression equation of the plotted data; (d) program code for applying a transformation to normalize distribution if the initial distribution is significantly skewed; and (e) program code for selecting the linear portion of the curve to determine a reference interval for the analyte in the reference population.

Thus, in some aspects, the invention provides computer readable media for indirectly determining a reference interval. Some embodiments of computer readable media include: program code for accepting user input parameters for selecting and loading selected analyte measurement data from a reference population in an existing database; program code for plotting cumulative frequencies from a plurality of biological samples against analyte measurements; program code for calculating a linear regression equation of the plotted data; and program code for determining a reference interval.

The computer readable media may also include program code for omitting outliers after initially loading and plotting frequencies for all data associated with the reference population. The computer readable media may also include program code for transforming data having non-Gaussian distribution to Gaussian distribution and program code for accepting an input for calculating maximum allowable error to account for biologic variation of analytes. The computer readable media may also include program code for calculating standard deviation, mean, median, and mode for all the data from the reference population and from the linear portion of the data only. It also optionally includes program code for comparing the newly derived reference interval to previously reported reference intervals for that analyte (e.g. calculating percentage of results above and below the old and new reference intervals).

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Some embodiments of suitable computing devices may comprise or be in communication with a number of external or internal devices such as a mouse, a CD-ROM, DVD, a keyboard, a display, audio speakers, one or more microphones, or any other input or output devices.

Any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

In some embodiments, the computer readable media may comprise: (a) program code for loading selected analyte measurement data from a specific reference population in an existing database and ability to filter the results by variable specific to a subject population, such as, but not limited to age, gender, laboratory location, ordering account number; further filtering capability allows inclusion of data only where the test of interest is ordered in conjunction with a specific second test and where the results meet predefined criteria (e.g. within the certain range); (b) program code for plotting cumulative frequencies of the data against the analyte measurements; and (c) program code for calculating a linear regression equation of the plotted data.

In some embodiments, the computer readable media may additionally comprise program code for restricting maximum allowable error to account for any known individual biological variation for the analyte in the selection of the linear portion of data after linear regression. In some embodiments, the computer readable media may additionally comprise program code for determining the reference interval and displaying the regression statistics used for its calculation.

In some embodiments, the computer readable media may additionally comprise program code for calculating confidence intervals for the limits of the reference interval. In some embodiments, the computer readable media may additionally comprise program code for calculating percentage of results that fall above and below the limits of the old (or existing) reference interval and above and below the limits of the new calculated reference interval. In some embodiments, the computer readable media may additionally comprise program code for removing the outlying observations and displaying the number of outliers removed. In some embodiments, the computer readable media may additionally comprise program code for calculating and displaying the percentage of the data in the linear range. In some embodiments, the computer readable media may additionally comprise calculating and displaying the start and end cut points of the linear range. In some embodiments, the computer readable media may additionally comprise program code for calculating the percentage of the data within the calculated reference interval as compared to the percentage of the data within a previously utilized reference interval. In some embodiments, the computer readable media may additionally comprise program code for calculating mean, median, and standard deviation of all data. In some embodiments, the computer readable media may additionally comprise mean, median, standard deviation, and mode of the linear region of the data.

Systems

In some aspects, the invention provides a system for determining a reference interval, comprising: (a) a component for pooling data from an existing database of measurements of the analyte from a selected reference population; (b) a component for plotting cumulative frequencies of data against a range of analyte measurements from the data of the selected reference population to determine a distribution of the data; (c) a component for applying a transformation to normalize data if the distribution is significantly skewed; (d) a component for calculating a linear regression of the plotted data; and (e) a component for determining a reference interval for the analyte in the reference population by selecting a range that corresponds to the linear portion of the curve.

Figure 3:
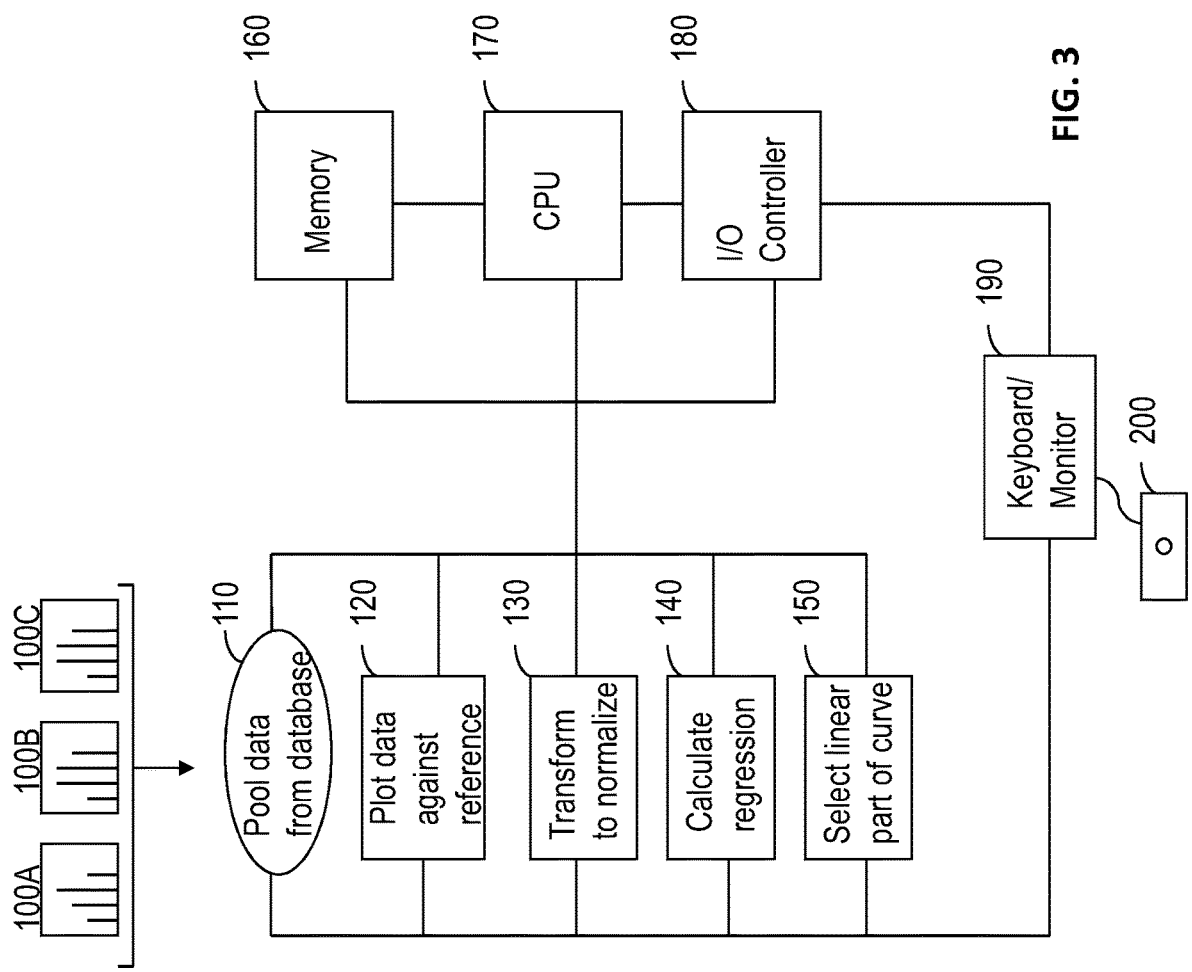
FIG. 3 is a schematic illustration of a system for determining a reference interval according to an embodiment of the invention.

FIG. 3 shows an embodiment of the flow of information in a system comprising the software of the present invention. As discussed above, a computer processor or CPU may include, for example, digital logic processors capable of processing input, executing algorithms, and generating output as necessary in response to the inputs received from the touch-sensitive input device. As detailed herein, such processors may include a microprocessor, such as an ASIC, and state machines, and/or other components. Such processors include, or may be in communication with, media, for example computer-readable media, which stores instructions that, when executed by the processor, cause the processor to perform the steps described herein.

Thus, in an embodiment, the starting point may comprise data generated from a plurality of assays for a particular analyte (illustrated here as 3 separate assay results 100A, 100B, and 100C). Once the data has been collected (110), it may be compiled and frequencies plotted against the range of values represented (120). In some embodiments, the data are transformed (130) if necessary using any standard spreadsheet software such as Microsoft Excel, FoxPro, Lotus, or the like. In some embodiments, the linear regression is calculated (140), such that a reference interval may be determined from the linear part of the curve (150). In some embodiments, data from previous runs are stored in the computer memory (160) and used as required.

At each point in the analysis, the user may input instructions via a keyboard (190), floppy disk, remote access (e.g., via the internet) (200), or other access means. The user may enter instructions including options for the run, how reports should be printed out, and the like. Also, at each step in the analysis, the data may be stored in the computer using a storage device common in the art such as disks, drives or memory (160). As is understood in the art, the processor (170) and I/O controller (180) are required for multiple aspects of computer function. Also, in an embodiment, there may be more than one processor.

In some cases, the user, via the keyboard (190), floppy disk, or remote access (200), may want to input variables or constraints for the analysis, as for example, a threshold for determining sufficient normalization of data.

Use of Newly Determined Reference Intervals

In some embodiments, newly determined reference intervals (i.e., "new" reference intervals) will differ substantially from reference intervals previously reported to healthcare providers (i.e., "old" reference intervals) and used by healthcare providers in interpretation of individual patient results for the same analyte. In such embodiments, especially where individual patient results fall within the ranges between the upper or lower limits of the old reference interval and outside the new reference interval, or vice versa, the healthcare provider may determine a diagnosis, prognosis, or recommended course of treatment for a medical condition that differs from the diagnosis, prognosis or recommended course of treatment the provider would have determined using the old reference interval.

Embodiments of the invention utilize automated large existing clinical laboratory databases in conjunction with application of statistical methods to remove subjectivity and allow inexpensive determination of reference intervals that are robust, accurate, and reproducible. Aspects of the invention also allow utilization of data with a non-Gaussian distribution, the ability to account for biologic variation of analytes, and the ability to calculate highly specific or individualized reference intervals based on desired subject characteristics. The large number of outpatient samples available in clinical laboratory databases alleviates additional problems, such as the number of samples available from age groups that are especially difficult to recruit for study (e.g. pediatric) and sample types that are more difficult to obtain (e.g. cerebrospinal fluid).

The present invention, among other benefits, addresses the need for inexpensive and reliable methods for determining reliable reference intervals through indirect sampling of the entire, mostly outpatient population represented in a large clinical laboratory database. Embodiments of the method further modify Hoffmann's method (rather than limited direct sampling of purportedly "healthy" populations or sampling hospital-based populations). Determination of new reference intervals according to embodiments of the invention unexpectedly allows reflection of the healthy population within the entire population. The ease and reduced cost of generating reliable reference intervals according to the invention will substantially improve patient care.

Based on the disclosure and teachings provided herein, persons of ordinary skill in the relevant arts will appreciate other ways and/or methods to implement the various embodiments.

EXAMPLES

The following Examples illustrate certain embodiments of the invention. The Examples are not intended to serve as a source of limitations to be imposed on the claims. The Examples merely illustrate embodiments that fall within the scope of certain aspects of the invention. The abbreviation "RI" means reference interval, and "CI" means confidence interval.

Example 1: Eosinophils in Subjects 13-18 Years Old by Cooks Distance (Tables 1-2) and Exhaustive Search Strategy (Tables 3-4)

TABLE 1

Eosinophils, 13-18 years old, Cooks Distance search strategy
Input Parameters:

| | |
|---|---|
| Title: | Eosinophils % Both Genders 13-18 Years Old |
| Precision: | Round to 2 number of decimal places |
| Max Residual Method: | specified fraction 21 of median |
| Search Strategy: | Cooks Distance |
| Boxcox: | No |

TABLE 2

Results for Eosinophils, 13-18 years old, Cooks Distance search strategy
Results:

| | |
|---|---|
| Size of data: | 10101 |
| Number of outliers: | 161 |
| Maximum Error Threshold: | 0.42 |
| Maximum Error: | 0.219 |
| % of data in linear range: | 2.817 |
| Start cut point: | 97.183 |
| End cut point: | 100 |
| RI: | [−90.547, 8.183] |
| Regression: | y = (1.039)x + (−93.145) |
| CI: | [−141.897, −39.197], [6.748, 9.617] |

TABLE 2-continued

Results for Eosinophils, 13-18 years old, Cooks Distance search strategy
Results:

| | |
|---|---|
| % of data in calculated RI: | 95.634 |
| % of data above the upper limit of calculated RI: | 4.366 |
| % of data below the lower limit of calculated RI: | 0 |
| % of data in old RI: | N/A |
| % of data above the upper limit of old RI: | N/A |
| % of data below the lower limit of old RI: | N/A |
| Mean of all data: | 3.233 |
| Median of all data: | 2 |
| SD of all data: | 2.536 |
| Mean (linear region): | 9.025 |
| Median (linear region): | 9 |
| SD (linear region): | 1.052 |
| Mode (linear region): | 8 |

TABLE 3

Eosinophils, 13-18 years old, exhaustive search strategy
Input Parameters:

| | |
|---|---|
| Title: | Eosinophils % Both Genders 13-18 Years Old |
| Precision: | Round to 2 number of decimal places |
| Max Residual Method: | specified fraction 21 of median |
| Search Strategy: | Exhaustive |
| Boxcox: | No |

TABLE 4

Results for Eosinophils, 13-18 years old, exhaustive search strategy
Results:

| | |
|---|---|
| Size of data: | 10101 |
| Number of outliers: | 161 |
| Maximum Error Threshold: | 0.42 |
| Maximum Error: | 0.29 |
| % of data in linear range: | 59.678 |
| Start cut point: | 21.489 |
| End cut point: | 81.167 |
| RI: | [−0.093, 4.5] |
| Regression: | y = (0.048)x + (−0.214) |
| CI: | [−2.471, 2.285], [2.393, 6.607] |
| % of data in calculated RI: | 79.873 |
| % of data above the upper limit of calculated RI: | 20.127 |
| % of data below the lower limit of calculated RI: | 0 |
| % of data in old RI: | N/A |
| % of data above the upper limit of old RI: | N/A |
| % of data below the lower limit of old RI: | N/A |
| Mean of all data: | 3.233 |
| Median of all data: | 2 |
| SD of all data: | 2.536 |
| Mean (linear region): | 2.233 |
| Median (linear region): | 2 |
| SD (linear region): | 0.991 |
| Mode (linear region): | 2 |

Figure 5B:
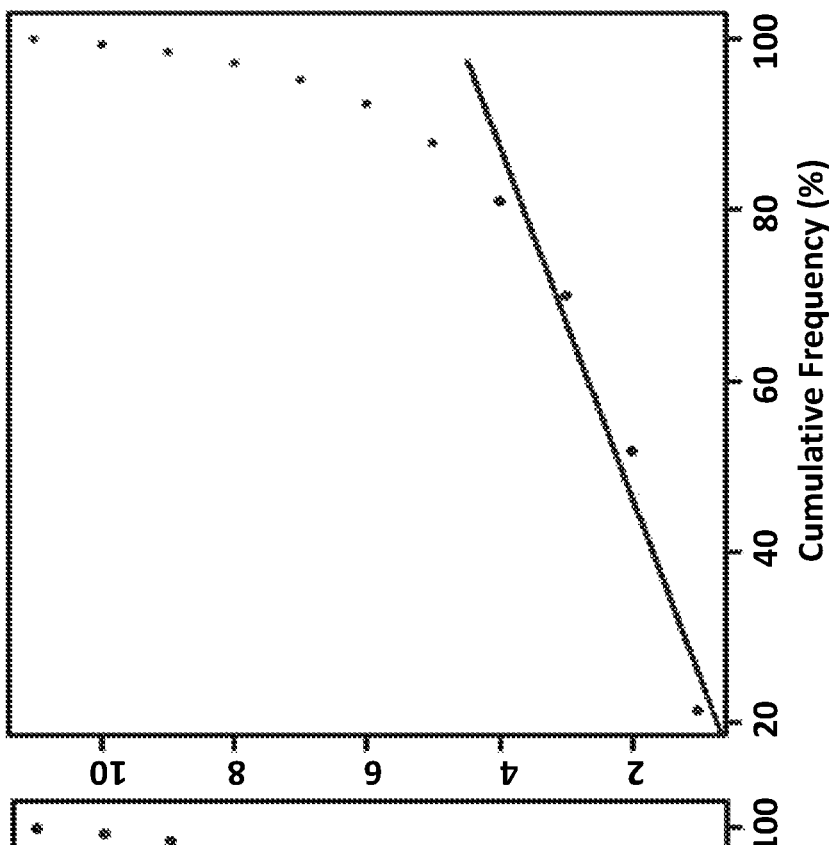
FIG. 5A-5B is a graphical illustration of determination of a reference interval for eosinophils in subjects 13-18 years old in Example 1 according to embodiments of the invention, showing linear regression by Cooks Distance in FIG. 5A and by exhaustive search method in FIG. 5B.
Figure 5A:
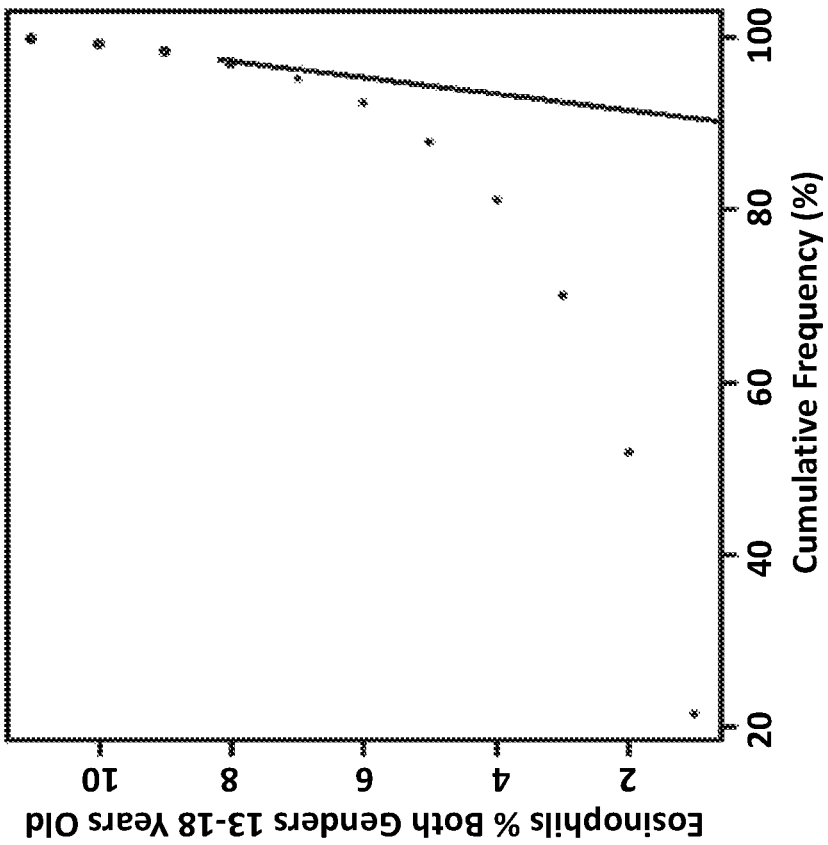

FIG. 4 shows the dot plot of all data initially loaded from the database for eosinophils in subjects 13-18 years old (4A) and the dot plot of data after removal of outliers according to Chauvenet criteria (4B). FIG. 5 shows the linear regression of the data by Cooks Distance (5A), and using exhaustive search strategy (5B). Thus, it can be seen that removal of outliers from a large dataset (here, removal of 161 outliers from a dataset of 10,101) generates an appropriate graphical representation for the selected population. This experiment also demonstrates the difference in results for using Cook's Distance as compared to an exhaustive search strategy to generate an appropriate reference interval for the population.

Example 2: Hemoglobin in High and Low Altitudes for Subjects 8-30 Days Old

TABLE 5

High-altitude hemoglobin (DV, NV, SV)

| | |
|---|---|
| Title: | Hemoglobin 8-30 Days Old High Altitude Locations |
| Precision: | Round to 2 number of decimal places |
| Max Residual Method: | specified fraction 2.8 of median |
| Search Strategy: | Cooks Distance |
| Boxcox: | No |

TABLE 6

Results for high-altitude hemoglobin
Results:

| | |
|---|---|
| Size of data: | 129 |
| Number of outliers: | 1 |
| Maximum Error Threshold: | 0.424 |
| Maximum Error: | 0.382 |
| % of data in linear range: | 88.281 |
| Start cut point: | 5.469 |
| End cut point: | 93.75 |
| RI: | [11.326, 18.917] |
| Regression: | y = (0.08)x + (11.126) |
| CI: | [10.977, 11.674], [18.569, 19.266] |
| % of data in calculated RI: | 86.822 |
| % of data above the upper limit of calculated RI: | 6.977 |
| % of data below the lower limit of calculated RI: | 6.202 |
| % of data in old RI: | N/A |
| % of data above the upper limit of old RI: | N/A |
| % of data below the lower limit of old RI: | N/A |
| Mean of all data: | 15.126 |
| Median of all data: | 15.1 |
| SD of all data: | 2.65 |
| Mean (linear region): | 15.12 |
| Median (linear region): | 15.1 |
| SD (linear region): | 2.051 |
| Mode (linear region): | 12.9 |

TABLE 7

Low-altitude hemoglobin (CB, DA, BN, HD, KC, MB, MB, PD, RN, SE, SO, SO, TA)
Input Parameters:

| | |
|---|---|
| Title: | Hemoglobin(hgb)-All-1wk-1mon-11.13.2012 |
| Precision: | Round to 2 number of decimal places |
| Max Residual Method: | specified fraction 2.8 of median |
| Search Strategy: | Cooks Distance |
| Boxcox: | No |
| Old RI: | [10.53, 16.27] |

TABLE 8

Results for low-altitude hemoglobin
Results:

| | |
|---|---|
| Size of data: | 1623 |
| Number of outliers: | 3 |
| Maximum Error Threshold: | 0.37 |
| Maximum Error: | 0.369 |
| % of data in linear range: | 81.481 |
| Start cut point: | 5.864 |
| End cut point: | 87.346 |
| RI: | [10.042, 16.438] |
| Regression: | y = (0.067)x + (9.874) |
| CI: | [9.717, 10.367], [16.111, 16.766] |

TABLE 8-continued

Results for low-altitude hemoglobin
Results:

| | |
|---|---|
| % of data in calculated RI: | 83.118 |
| % of data above the upper limit of calculated RI: | 10.351 |
| % of data below the lower limit of calculated RI: | 6.531 |
| % of data in old RI: | 77.449 |
| % of data above the upper limit of old RI: | 12.015 |
| % of data below the lower limit of old RI: | 10.536 |
| Mean of all data: | 13.391 |
| Median of all data: | 13.2 |
| SD of all data: | 2.406 |
| Mean (linear region): | 13.04 |
| Median (linear region): | 13 |
| SD (linear region): | 1.563 |
| Mode (linear region): | 12 |

Figure 6A:
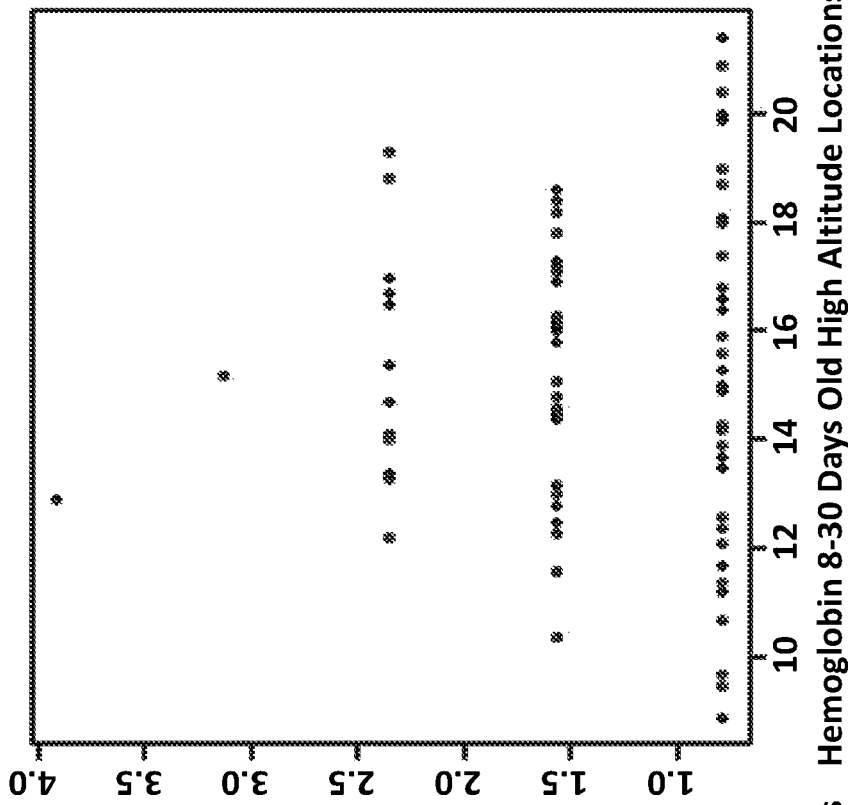
FIG. 6A-6B is a graphical illustration of data for hemoglobin at high altitudes (subjects 8-30 days old) in Example 2 according to an embodiment of the invention, where
Figure 6B:
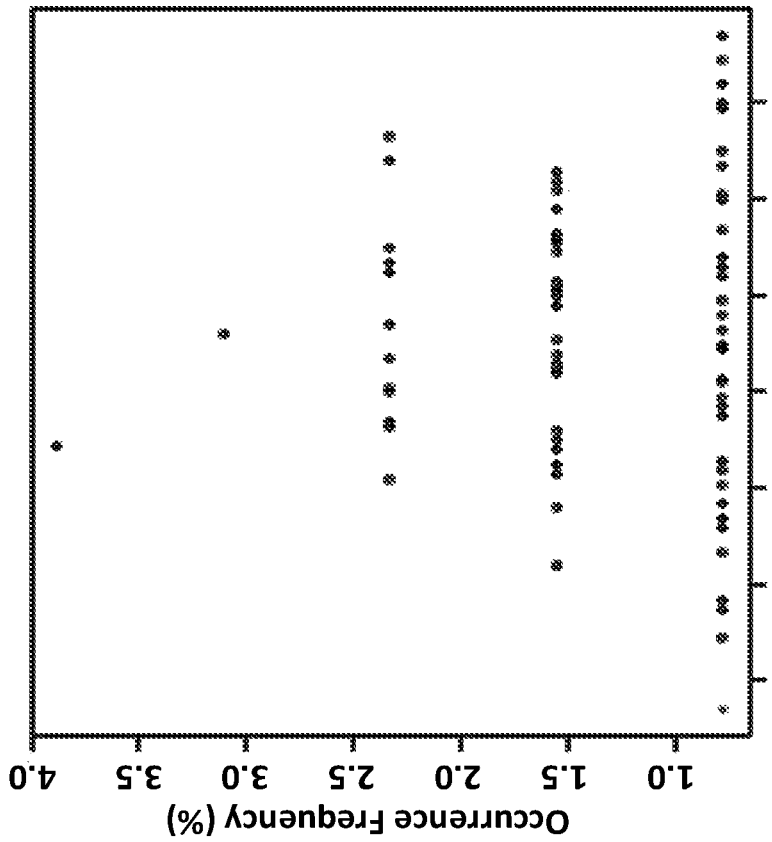
Figure 7A:
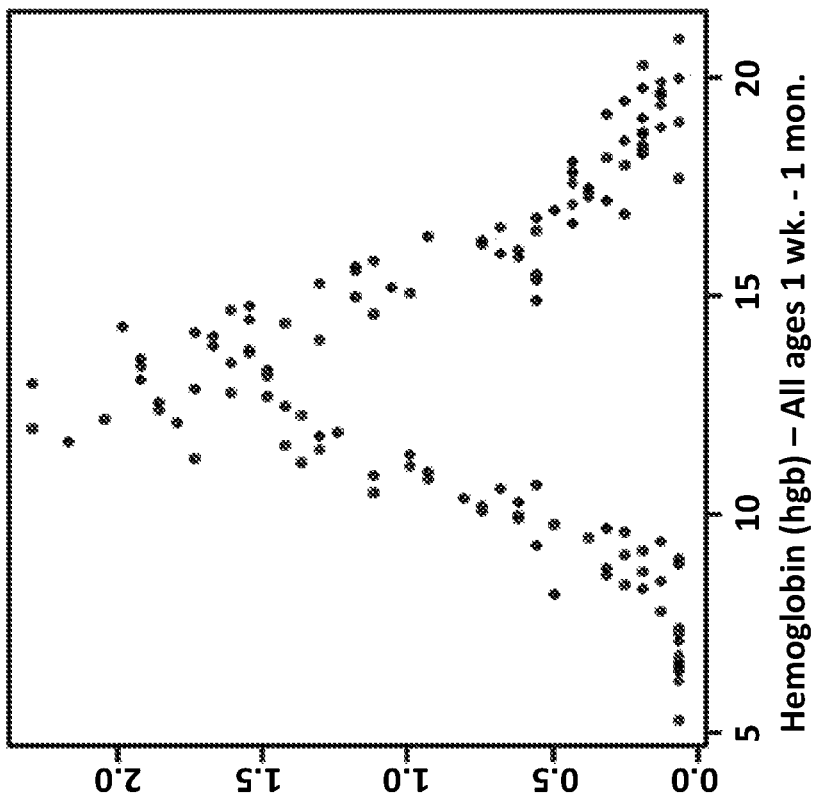
FIG. 7A-7B is a graphical illustration of data for hemoglobin at low altitudes (subjects 8-30 days old) in Example 2 according to an embodiment of the invention, where
Figure 7B:
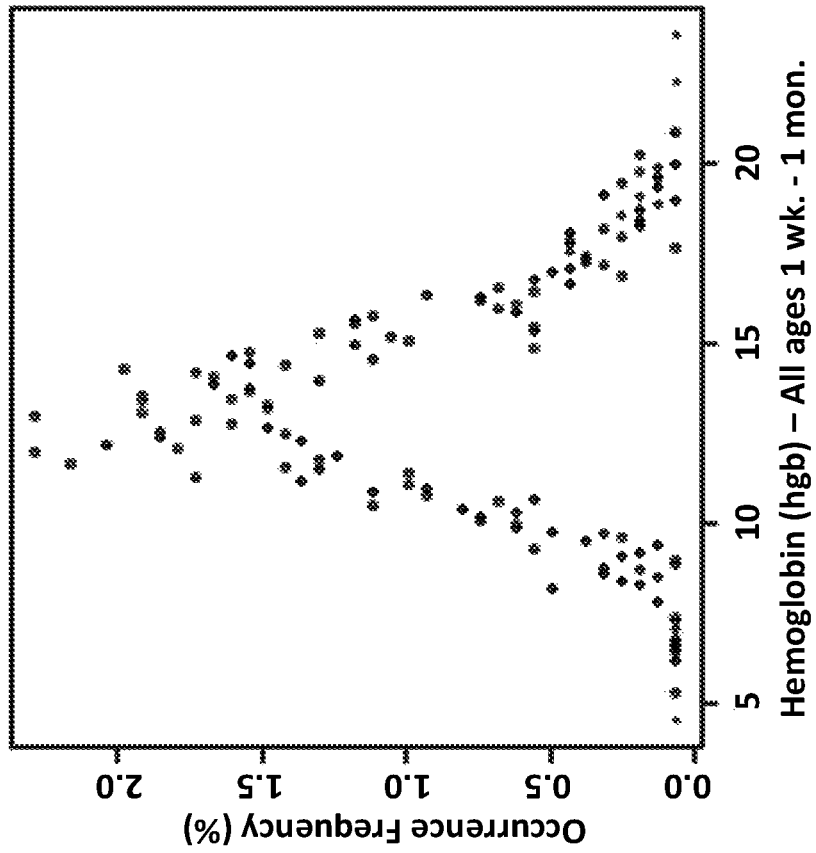
Figure 8A:
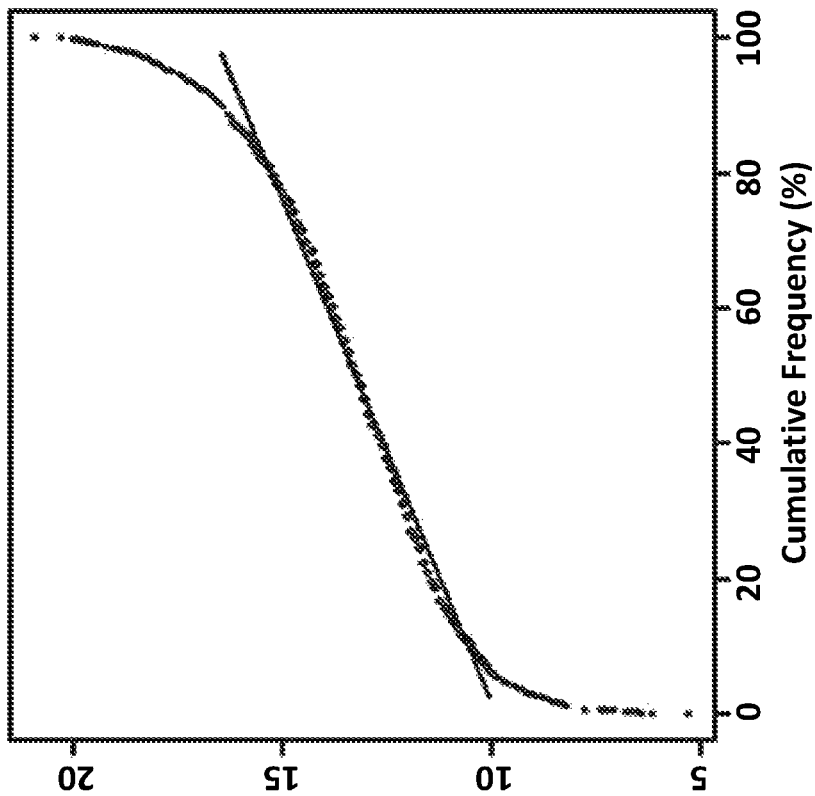
FIG. 8A-8B is a graphical illustration of determination of reference intervals for hemoglobin at high (FIG. 8A) and low (FIG. 8B) altitudes in Example 2 according to embodiments of the invention.
Figure 8B:
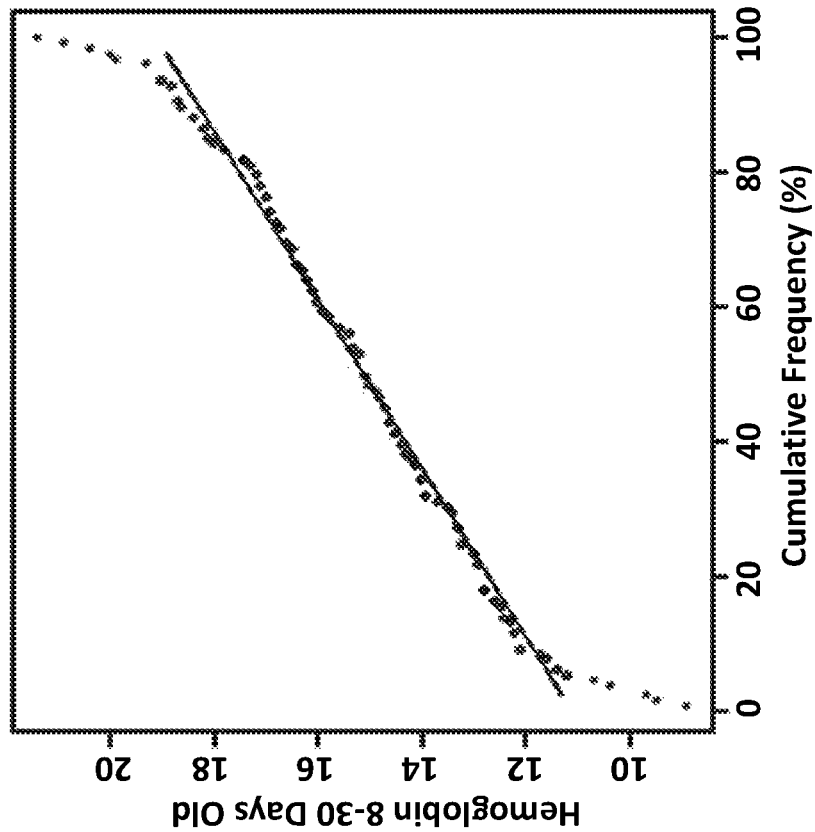

FIG. 6 shows the dot plot of all data initially loaded from the database for hemoglobin in high altitudes before (6A) and after (6B) removal of outliers according to Chauvenet criteria. FIG. 7 shows the dot plot of all data initially loaded from the database for hemoglobin in low altitudes before (7A) and after (7B) removal of outliers according to Chauvenet criteria. FIG. 8 shows the linear regressions of the data in FIGS. 6-7 (Tables 5-8). Thus it was found that confidence intervals do not overlap for high-altitude versus low-altitude reference interval limits, corresponding to the statistically significant difference in hemoglobin values between high altitude and low altitude locations. This shows that reference intervals generated for a specific sub-population may be substantially different depending on the characteristic selected (here, geographic location) and may be also be different from a previously utilized reference interval.

Example 3: Platelets in Subjects 18-100 Years Old Determined at Two Time Points

Platelet counts ($\lambda 10^3$ per $\mu L$) were sampled for all subjects 18-100 years old who were tested through an early time point (Tables 9-10) or a later time point (Tables 11-12) selected as the reference population.

TABLE 9

Platelets in subjects sampled at earlier time point
Input Parameters:

| | |
|---|---|
| Title: | Platelets-Both Genders 18yrs-100yrs-11.13.12 |
| Precision: | Round to 1 number of decimal places |
| Max Residual Method: | specified fraction 9.1 of median |
| Search Strategy: | Cooks Distance |
| Boxcox: | No |
| Old RI: | [140, 415] |

TABLE 10

Results for platelets at earlier time point
Results:

| | |
|---|---|
| Size of data: | 13222 |
| Number of outliers: | 52 |
| Maximum Error Threshold: | 23.205 |
| Maximum Error: | 22.814 |
| % of data in linear range: | 92.498 |
| Start cut point: | 2.149 |
| End cut point: | 94.647 |
| RI: | [154.571, 359.429] |
| Regression: | y = (2.156)x + (149.18) |

TABLE 10-continued

Results for platelets at earlier time point
Results:

| | |
|---|---|
| CI: | [135.124, 174.019], [339.97, 378.887] |
| % of data in calculated RI: | 87.241 |
| % of data above the upper limit of calculated RI: | 8.093 |
| % of data below the lower limit of calculated RI: | 4.666 |
| % of data in old RI: | 94.464 |
| % of data above the upper limit of old RI: | 2.677 |
| % of data below the lower limit of old RI: | 2.859 |
| Mean of all data: | 261.119 |
| Median of all data: | 255 |
| SD of all data: | 73.459 |
| Mean (linear region): | 254.025 |
| Median (linear region): | 252 |
| SD (linear region): | 54.119 |
| Mode (linear region): | 270 |

TABLE 11

Platelets in subjects sampled at later time point
Input Parameters:

| | |
|---|---|
| Title: | Platelets Both Genders 18-100 Years Old Later Data |
| Precision: | Round to 1 number of decimal places |
| Max Residual Method: | specified fraction 9.1 of median |
| Search Strategy: | Cooks Distance |
| Boxcox: | No |

TABLE 12

Results for platelets at later time point
Results:

| | |
|---|---|
| Size of data: | 74571 |
| Number of outliers: | 234 |
| Maximum Error Threshold: | 23.023 |
| Maximum Error: | 22.996 |
| % of data in linear range: | 91.942 |
| Start cut point: | 2.097 |
| End cut point: | 94.039 |
| RI: | [152.869, 358.74] |
| Regression: | y = (2.167)x + (147.452) |
| CI: | [133.446, 172.292], [339.303, 378.177] |
| % of data in calculated RI: | 86.956 |
| % of data above the upper limit of calculated RI: | 8.573 |
| % of data below the lower limit of calculated RI: | 4.471 |
| % of data in old RI: | N/A |
| % of data above the upper limit of old RI: | N/A |
| % of data below the lower limit of old RI: | N/A |
| Mean of all data: | 260.304 |
| Median of all data: | 253 |
| SD of all data: | 74.252 |
| Mean (linear region): | 252.074 |
| Median (linear region): | 250 |
| SD (linear region): | 54.026 |
| Mode (linear region): | 236 |

Figure 9B:
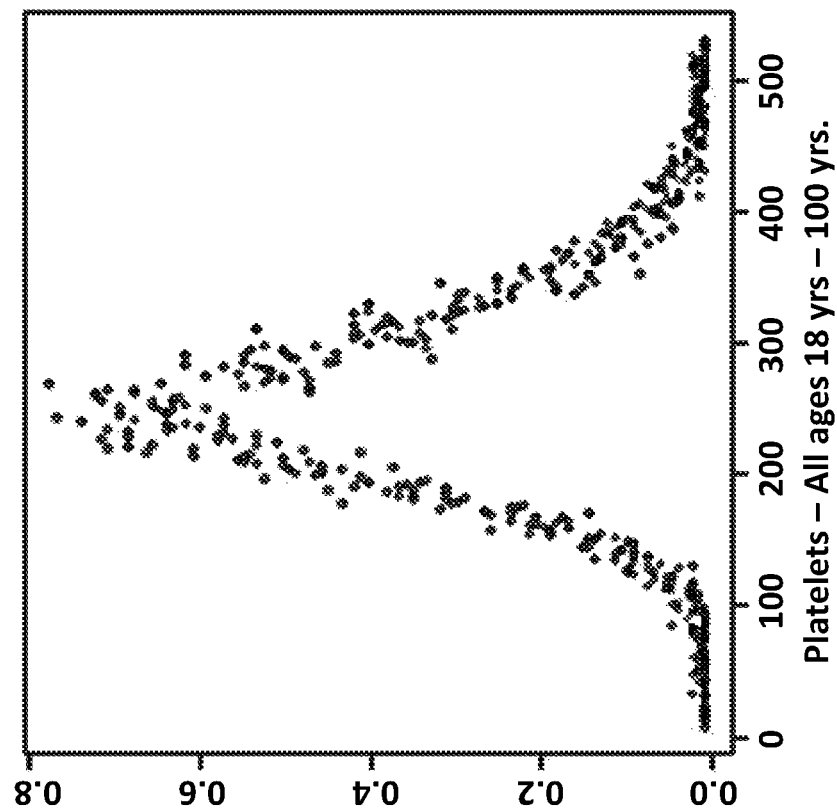
FIG. 9A-9B is a graphical illustration of data for platelets in subjects age 18-100 years old in Example 3 according to an embodiment of the invention, where the data is selected from the database at an early time point.
Figure 9A:
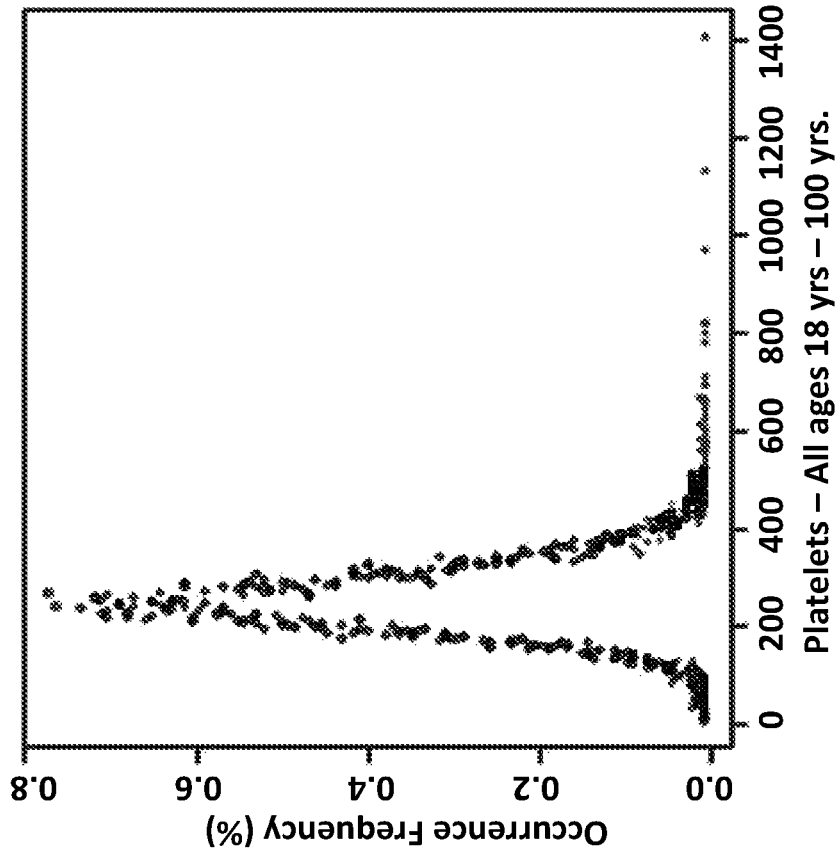
Figure 11B:
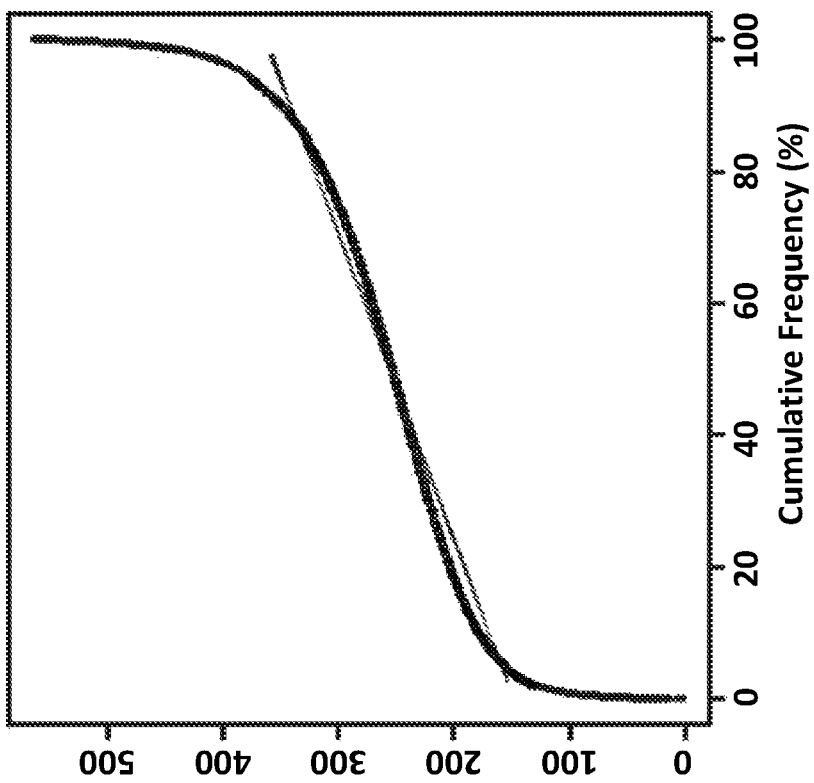
FIG. 11A-11B is a graphical illustration of determination of reference intervals for platelets in subjects 18-100 years old in Example 3 according to embodiments of the invention.
Figure 11A:
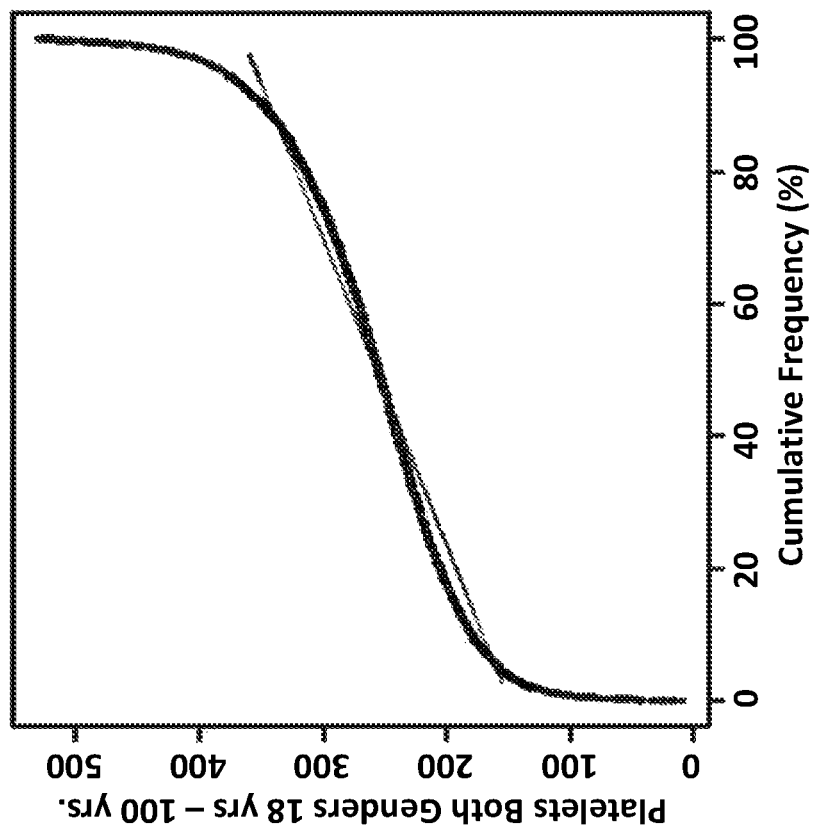

FIG. 9 shows the dot plot of all data initially loaded from the database for the early time point of platelets in subjects 18-100 years old before (9A) and after (9B) removal of outliers according to Chauvenet criteria. FIG. 10 shows the dot plot of all data loaded from the database for the later time point of platelets in subjects 18-100 years old before (10A) and after (10B) removal of outliers according to Chauvenet criteria. FIG. 11 shows the linear regressions for the data in FIGS. 9-10 (Tables 9-12). The two datasets of 13,222 and 74,571 yield reference intervals that are not statistically different (both are within 95% CI of each other) but are both notably narrower than the old (previously utilized) reference interval. This experiment demonstrates that subjects with platelet measurements falling outside of the new reference intervals but within the old reference interval could receive a different diagnosis, prognosis, or treatment selection if their healthcare provider relied on the new interval rather than the old interval.

Example 4: Neutrophils in Subjects 13-18 Years Old, without and with BoxCox Transformation

TABLE 13

Neutrophils, without BoxCox transformation
Input Parameters:

| | |
|---|---|
| Title: | Neutrophils Absolute Both Genders 13-18 Years Old |
| Precision: | Round to 2 number of decimal places |
| Max Residual Method: | specified fraction 16.1 of median |
| Search Strategy: | Cooks Distance |
| Boxcox: | No |

TABLE 14

Neutrophils results without BoxCox transformation
Results:

| | |
|---|---|
| Size of data: | 56468 |
| Number of outliers: | 349 |
| Maximum Error Threshold: | 0.58 |
| Maximum Error: | 0.555 |
| % of data in linear range: | 90.071 |
| Start cut point: | 0.116 |
| End cut point: | 90.187 |
| RI: | [1.279, 6.229] |
| Regression: | y = (0.052)x + (1.149) |
| CI: | [0.751, 1.807], [5.697, 6.761] |
| % of data in calculated RI: | 86.738 |
| % of data above the upper limit of calculated RI: | 11.651 |
| % of data below the lower limit of calculated RI: | 1.612 |
| % of data in old RI: | N/A |
| % of data above the upper limit of old RI: | N/A |
| % of data below the lower limit of old RI: | N/A |
| Mean of all data: | 4.041 |
| Median of all data: | 3.6 |
| SD of all data: | 1.991 |
| Mean (linear region): | 3.551 |
| Median (linear region): | 3.4 |
| SD (linear region): | 1.255 |
| Mode (linear region): | 3 |

TABLE 15

Neutrophils with BoxCox transformation
Input Parameters:

| | |
|---|---|
| Title: | Neutrophils Absolute Both Genders 13-18 Years Old |
| Precision: | Round to 2 number of decimal places |
| Max Residual Method: | specified fraction 16.1 of median |
| Search Strategy: | Cooks Distance |
| Boxcox: | Yes |

TABLE 16

Neutrophils results with BoxCox transformation
Results:

| | |
|---|---|
| Size of data: | 56468 |
| Number of outliers: | 349 |

TABLE 16-continued

Neutrophils results with BoxCox transformation
Results:

| | |
|---|---|
| Maximum Error Threshold: | 0.294 |
| Maximum Error: | 0.286 |
| % of data in linear range: | 91.855 |
| Start cut point: | 2.199 |
| End cut point: | 94.054 |
| RI: | [0.504, 3.178] |
| Regression: | y = (0.028)x + (0.433) |
| Boxcox: | c = 0, $\lambda$ = 0.5 |
| inversed RI: | [1.567, 6.703] |
| CI: | [1.259, 1.909], [6.054, 7.384] |
| % of data in calculated RI: | 87.621 |
| % of data above the upper limit of calculated RI: | 8.649 |
| % of data below the lower limit of calculated RI: | 3.73 |
| % of data in old RI: | N/A |
| % of data above the upper limit of old RI: | N/A |
| % of data below the lower limit of old RI: | N/A |
| Mean of all data: | 4.041 |
| Median of all data: | 3.6 |
| SD of all data: | 1.991 |
| Mean (linear region): | 3.729 |
| Median (linear region): | 3.6 |
| SD (linear region): | 1.358 |
| Mode (linear region): | 3 |
| Mode (linear region, transformed): | 1.464 |

Figure 12B:
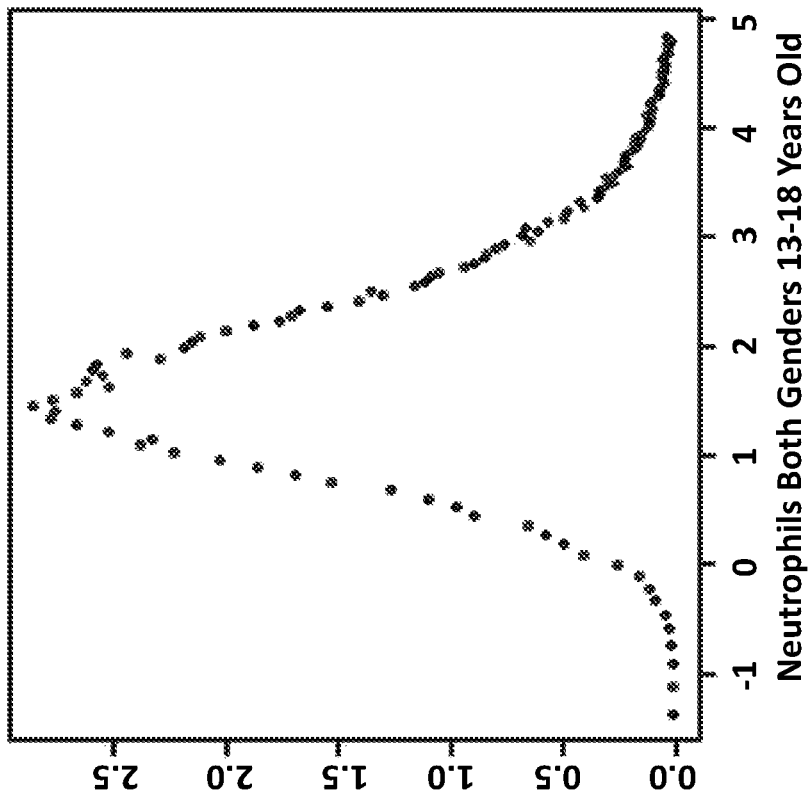
FIG. 12A-12B is graphical illustration of data for neutrophils in subjects 13-18 years old in Example 4 according to an embodiment of the invention.
Figure 12A:
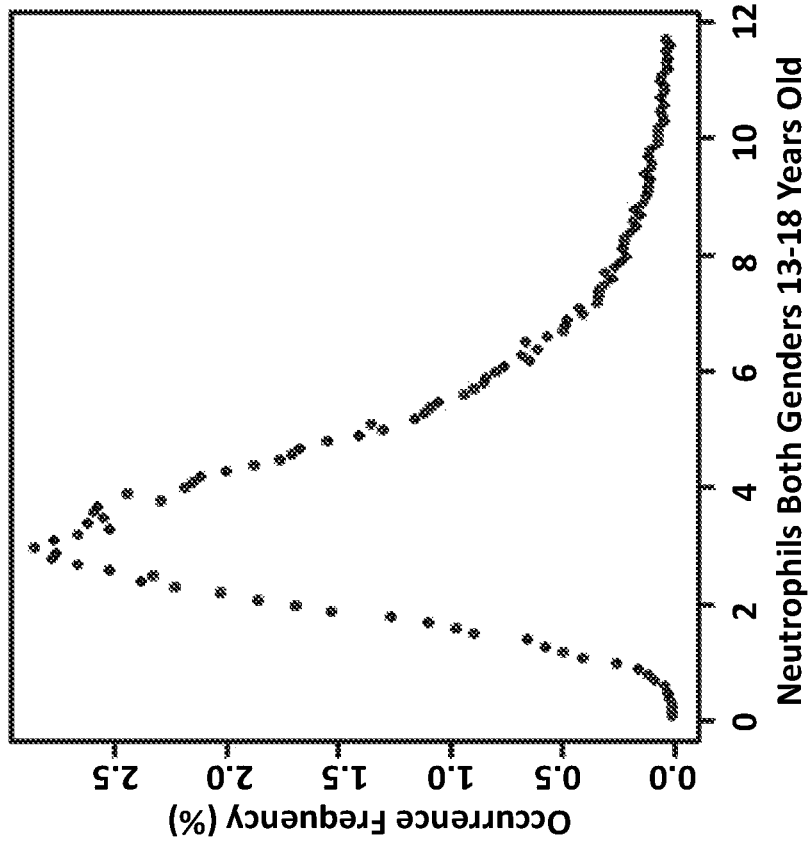
Figure 13A:
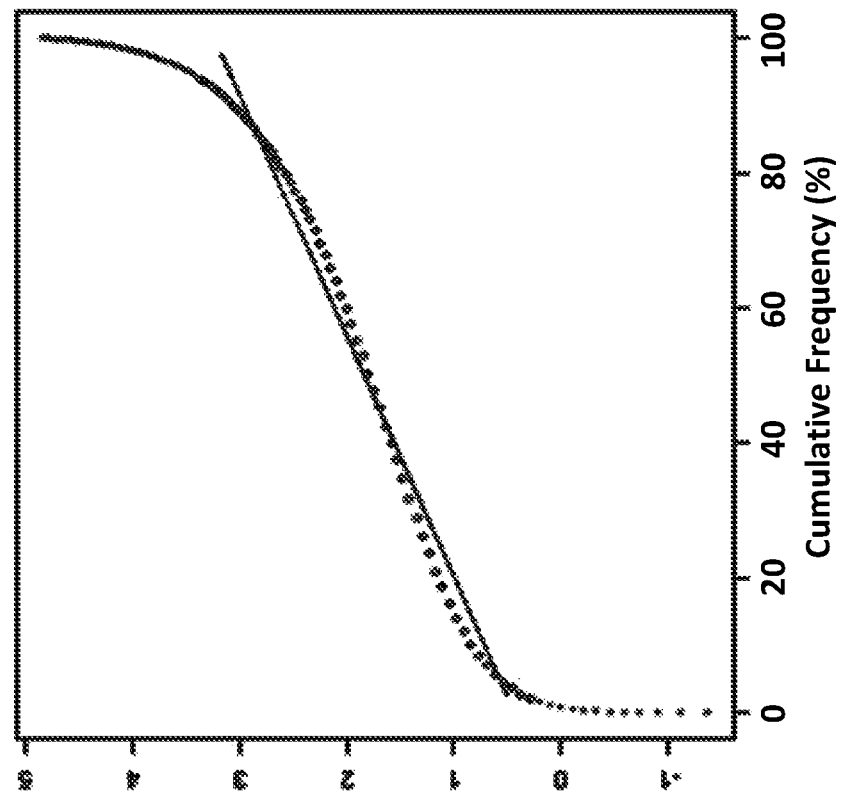
FIG. 13A-13B is graphical illustration of determination of reference intervals for neutrophils in subjects 13-18 years old in Example 4 according to embodiments of the invention.
Figure 13B:
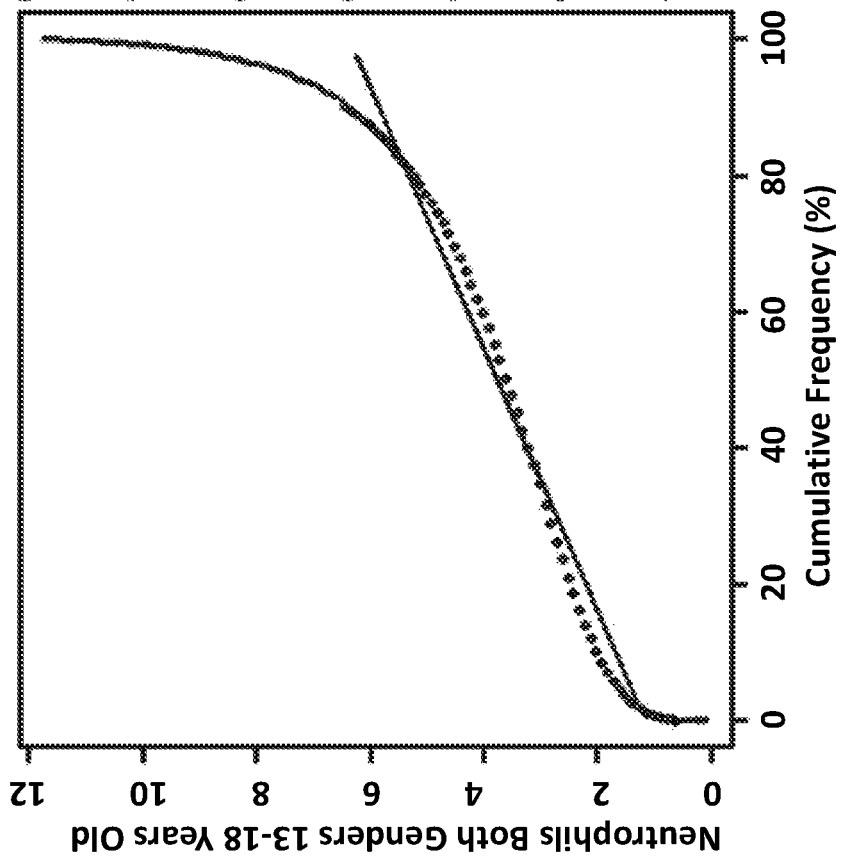

FIG. 12 shows the dot plot of data after outliers are removed for neutrophils in subjects 13-18 years old before (12A) and after (12B) BoxCox transformation. FIG. 13 shows the linear regression of the data in FIG. 12, with and without BoxCox transformation (Tables 12 and 14). Thus it can be seen that the transformation with BoxCox to achieve Gaussian distribution yields an improvement in the calculations.

Example 5: Thyroid-Stimulating Hormone (TSH) µIU/mL in all Subjects

Data (n=64,728) were loaded from six networked laboratory locations.

TABLE 17

TSH in all subjects
Input Parameters:

| | |
|---|---|
| Title: | TSH Data Comparison |
| Precision: | Round to 3 number of decimal places |
| Max Residual Method: | specified value 0.09 |
| Search Strategy: | Cooks Distance |
| Boxcox: | No |
| Old RI: | [0.44, 3.05] |

TABLE 18

Results for TSH in all subjects
Results:

| | |
|---|---|
| Size of data: | 64728 |
| Number of outliers: | 1732 |
| Maximum Error Threshold: | 0.09 |
| Maximum Error: | 0.09 |
| % of data in linear range: | 65.449 |
| Start cut point: | 6.305 |
| End cut point: | 71.754 |
| RI: | [0.441, 2.997] |
| Regression: | y = (0.027)x + (0.374) |
| CI: | [0.371, 0.512], [2.926, 3.067] |
| % of data in calculated RI: | 74.564 |

TABLE 18-continued

Results for TSH in all subjects
Results:

| | |
|---|---|
| % of data above the upper limit of calculated RI: | 19.475 |
| % of data below the lower limit of calculated RI: | 5.96 |
| % of data in old RI: | 75.275 |
| % of data above the upper limit of old RI: | 18.774 |
| % of data below the lower limit of old RI: | 5.951 |
| Mean of all data: | 2.498 |
| Median of all data: | 1.713 |
| SD of all data: | 5.217 |
| Mean (linear region): | 1.424 |
| Median (linear region): | 1.408 |
| SD (linear region): | 0.502 |
| Mode (linear region): | 0.952 |

Figure 15:
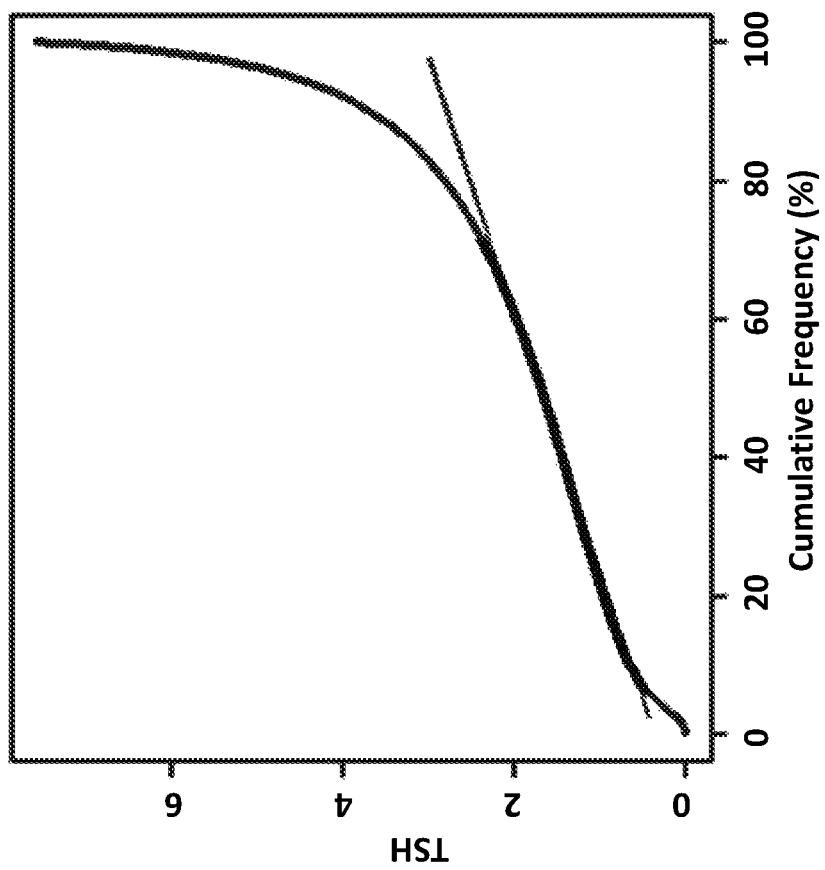
FIG. 15 is graphical illustration of linear regression for determination of a reference interval for thyroid stimulating hormone (TSH) in all subjects in Example 5 according to an embodiment of the invention.

FIG. 14 shows the dot plot of all data initially loaded from the database for TSH in all subjects before (14A) and after (14B) removal of outliers according to Chauvenet criteria. FIG. 15 shows the linear regression of the data in FIG. 14. This experiment demonstrates that in some cases the newly calculated RI may be similar to the previously utilized RI.

We claim:

1. A method for providing a reference interval for an analyte to evaluate a subject's test result for the analyte, the method comprising:
    (a) pooling data from a database in which measurements of the analyte from a reference population have been stored, wherein the reference population comprises both healthy and unhealthy subjects;
    (b) plotting cumulative frequencies of data against the measurements of the analyte from the reference population to form a distribution;
    (c) transforming the plotted data to normalize the distribution if the mean of the plotted data is located in the first or fifth quintile of the distribution, thereby resulting in transformed plotted data;
    (d) calculating a linear regression of the plotted data, or if transformed, of the transformed plotted data, resulting in a curve and a value for maximum residual error, wherein the linear regression is constrained so that the maximum residual error of the linear portion of the curve is below a predetermined threshold to account for a within-individual biological variation for the analyte; and
    (e) determining the reference interval for the analyte in the reference population by selecting a range that corresponds to the linear portion of the curve.

2. The method of claim 1, wherein the reference population comprises a characteristic of interest so as to generate a reference interval for use to evaluate test results of subjects having the characteristic of interest.

3. The method of claim 1, wherein the reference population includes at least 100, 120, 140, 160, 180, 200, 220, 240, 260, 280, 300, 320, 340, 360, 380, 400, 500, 600, 700, 800, 900, 1,000, 1,500, 2,000, 4,000, 6,000, 8,000, 10,000, 15,000, 20,000, 40,000, 60,000, 80,000, or 100,000 different individuals.

4. The method of claim 1, wherein transformation by a BoxCox method is applied if the mean of the data pooled from the database is located in the first or fifth quintile of the distribution.

5. The method of claim 4, wherein the linear regression is calculated by Cooks distance or an exhaustive search strategy.

6. The method of claim 1, wherein confidence intervals are calculated for the upper and lower limits of the reference interval.

7. The method of claim 1, wherein the linear regression is calculated by Cooks distance or an exhaustive search strategy.

8. A method of evaluating the subject's test result, the method comprising:
    (a) pooling data from a database in which measurements of the analyte from a reference population have been stored, wherein the reference population comprises both healthy and unhealthy subjects;
    (b) plotting cumulative frequencies of data against the measurements of the analyte from the reference population to form a distribution;
    (c) transforming the plotted data to normalize the distribution if the mean of the plotted data is located in the first or fifth quintile of the distribution, thereby resulting in transformed plotted data;
    (d) calculating a linear regression of the plotted data, or if transformed, of the transformed plotted data, resulting in a curve and a value for maximum residual error, wherein the linear regression is constrained so that the maximum residual error of the linear portion of the curve is below a predetermined threshold to account for a within-individual biological variation for the analyte; and
    (e) determining the reference interval for the analyte in the reference population by selecting a range that corresponds to the linear portion of the curve, and
    (f) determining a different course of treatment, diagnosis, or prognosis if the subject's test result for the analyte is outside the reference interval.

9. A non-transitory computer-readable media for determining a reference interval, the computer-readable media comprising:
    (a) program code for selecting analyte data for a specific reference population from an existing database;
    (b) program code for plotting cumulative frequencies of the data against a range of analyte measurements from a reference population to form a distribution;
    (c) program code for transforming the plotted data to normalize the distribution if the mean of the plotted data is located in the first or fifth quintile of the distribution, thereby resulting in transformed plotted data
    (d) program code for calculating a linear regression equation of the plotted data, or if transformed, of the transformed plotted data, resulting in a curve and a value for maximum residual error, wherein the linear regression is constrained so that the maximum residual error of the linear portion of the curve is below a predetermined threshold to account for a within-individual biological variation for the analyte;
    (e) program code for applying a transformation to normalize the distribution if the distribution is significantly skewed; and
    (f) program code for selecting the reference interval for the analyte in the reference population that corresponds to the linear portion of the curve.

10. The non-transitory computer-readable media of claim 9, further comprising program code for selecting data comprising one, two, or more required characteristics from the desired reference population.

11. The non-transitory computer-readable media of claim 9, the transforming the plotted data to normalize the distribution is by applying a BoxCox transformation.

12. The non-transitory computer-readable media of claim 9, wherein calculating linear regression is by Cooks distance or exhaustive search.

13. The non-transitory computer-readable media of claim 9, further comprising program code for calculating confidence intervals for the upper and lower limits of the determined reference interval.

14. The non-transitory computer-readable media of claim 9, further comprising program code for calculating a percentage of subjects in the reference population falling within the range that corresponds to the linear portion of the curve.

15. A system for determining a reference interval, comprising the non-transitory computer-readable media of claim 9;
(e).

16. The non-transitory computer-readable media of claim 9, further comprising program code for calculating the percentage of subjects in the reference population above and below previously utilized and newly calculated reference interval limits for the same analyte.

* * * * *